(12) United States Patent
Teague et al.

(10) Patent No.: US 7,727,227 B2
(45) Date of Patent: Jun. 1, 2010

(54) MEDICAL RETRIEVAL DEVICES WITH LASER AND RETRIEVAL ASSEMBLY

(75) Inventors: James A. Teague, Spencer, IN (US);
Jason W. Kear, Bloomington, IN (US);
Juli L. Curtis, Bloomington, IN (US);
Eric Cheng, Bloomington, IN (US);
Joseph W. Segura, Rochester, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1609 days.

(21) Appl. No.: 10/942,084

(22) Filed: Sep. 16, 2004

(65) Prior Publication Data

US 2005/0154378 A1 Jul. 14, 2005

Related U.S. Application Data

(60) Provisional application No. 60/503,807, filed on Sep. 18, 2003.

(51) Int. Cl.
*A61N 5/06* (2006.01)
*A61B 17/22* (2006.01)

(52) U.S. Cl. .............................. 606/2.5; 606/13; 606/14; 606/114

(58) Field of Classification Search ................... 606/2.5, 606/13–15, 113, 114, 205–207; 607/88–90, 607/92, 93
See application file for complete search history.

(56) References Cited

U.S. PATENT DOCUMENTS

| | | | |
|---|---|---|---|
| 5,192,286 A | | 3/1993 | Phan et al. |
| 5,376,094 A | | 12/1994 | Kline et al. |
| 5,445,608 A | * | 8/1995 | Chen et al. ..................... 604/20 |
| 5,520,697 A | | 5/1996 | Lindenberg et al. |
| 5,855,577 A | * | 1/1999 | Murphy-Chutorian et al. . 606/7 |
| 5,957,916 A | * | 9/1999 | Jeevanandam et al. ......... 606/15 |
| 6,099,534 A | * | 8/2000 | Bates et al. .................. 606/127 |
| 6,224,612 B1 | * | 5/2001 | Bates et al. .................. 606/114 |
| 6,264,664 B1 | | 7/2001 | Avellanet |
| 6,348,056 B1 | * | 2/2002 | Bates et al. .................. 606/114 |
| 6,416,519 B1 | | 7/2002 | VanDusseldorp |
| 6,419,679 B1 | | 7/2002 | Dhindsa |
| 6,500,182 B2 | | 12/2002 | Foster |
| 7,322,989 B2 | * | 1/2008 | Teague et al. ................ 606/114 |
| 2001/0041899 A1 | | 11/2001 | Foster |
| 2002/0026203 A1 | | 2/2002 | Bates et al. |
| 2002/0068944 A1 | | 6/2002 | White et al. |
| 2003/0093087 A1 | | 5/2003 | Jones et al. |
| 2004/0026942 A1 | | 2/2004 | Kessler et al. |
| 2004/0087971 A1 | | 5/2004 | Arnott |
| 2005/0154378 A1 | | 7/2005 | Teague et al. |

FOREIGN PATENT DOCUMENTS

| | | |
|---|---|---|
| DE | 86 26 340 4 | 2/1990 |
| DE | 197 22 429 A1 | 12/1998 |
| WO | WO 01/97699 A1 | 12/2001 |

OTHER PUBLICATIONS

Sep. 28, 2006 Office Action issued by U.S. Patent and Trademark Office in U.S. Appl. No. 10/942,105.
Communication relating to the Results of the Partial International Search Report from International Application No. PCT/US2004/026742.
Communication Relating to the Results of the Partial International Search from International Application No. PCT/US2004/026740.

\* cited by examiner

*Primary Examiner*—Ahmed M Farah
(74) *Attorney, Agent, or Firm*—Finnegan Henderson Farabow Garrett & Dunner, L.L.P.

(57) ABSTRACT

A medical device includes a sheath having a lumen and an elongate member disposed within the lumen of the sheath. The elongate member is moveable relative to the sheath and includes a retrieval assembly. The retrieval assembly has a collapsed position within the lumen of the sheath and an expanded position when extended beyond a distal end of the sheath. The elongate member defines a lumen configured to receive a laser.

29 Claims, 18 Drawing Sheets

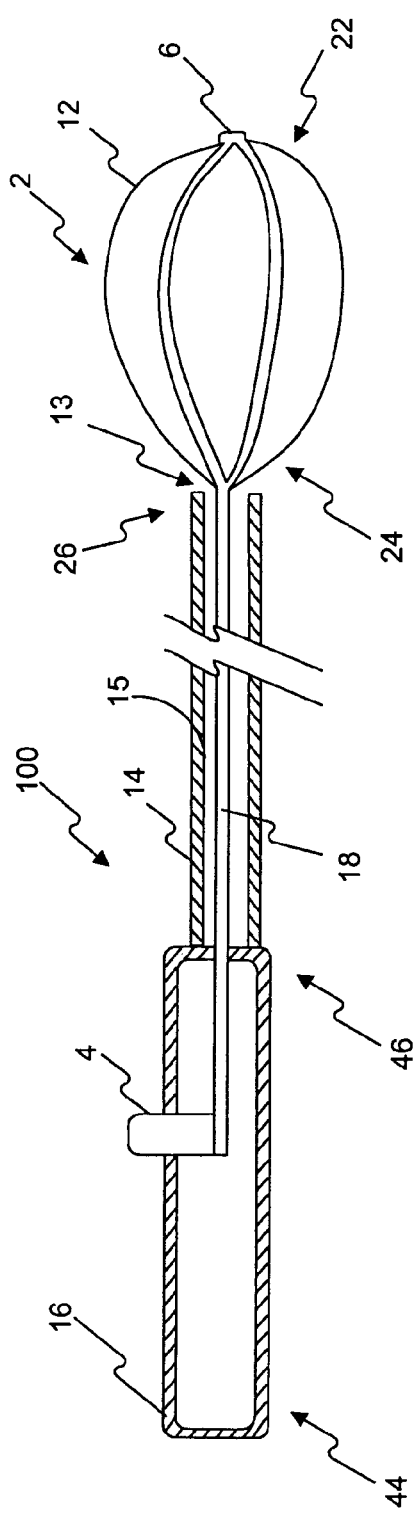
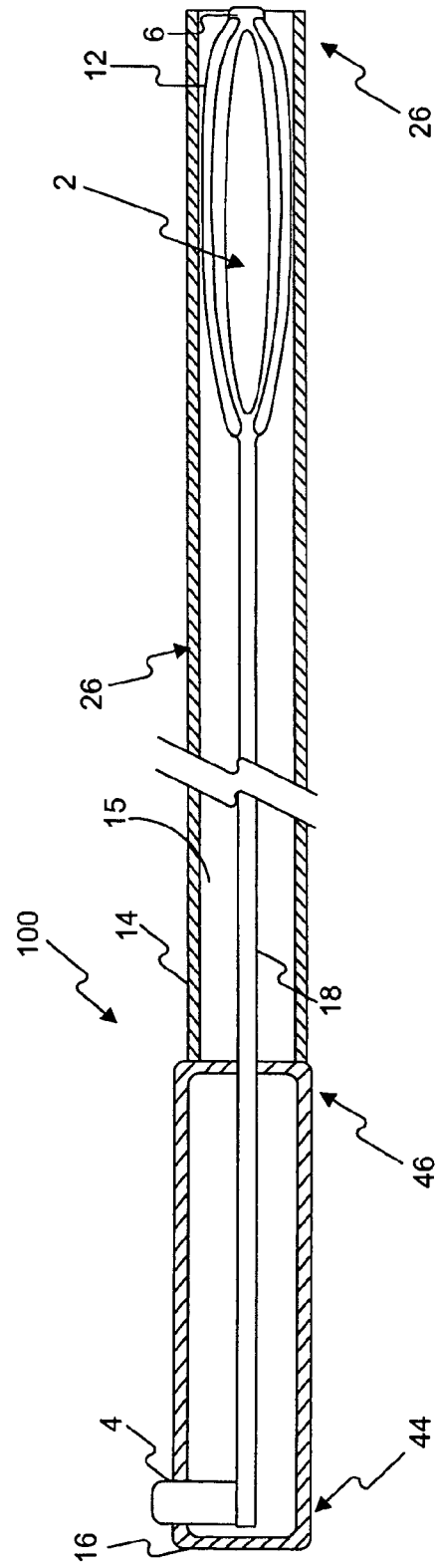

MEDICAL RETRIEVAL DEVICES WITH LASER AND RETRIEVAL ASSEMBLY

CLAIM FOR PRIORITY

This patent application claims the benefit of U.S. Provisional Application No. 60/503,807, filed Sep. 18, 2003.

FIELD OF THE INVENTION

This disclosure relates generally to medical devices and more particularly to medical retrieval devices.

BACKGROUND OF THE INVENTION

Certain medical procedures and treatments involve the use of retrieval devices with lasers and retrieval assemblies for breaking up and/or capturing material from an anatomical site in a patient, such as kidney stones and/or other materials. Commonly, these retrieval devices comprise a laser that directs energy at material at the anatomical site to break up the material.

SUMMARY OF THE INVENTION

Exemplary embodiments of the invention provide for a retrieval device that directs energy from a laser towards material within a patient's body at an acute angle to improve a user's ability to fragment and capture the material. Exemplary embodiments of the invention further provide methods for using the device to break apart and capture material from within the body of a patient.

According to one aspect, the invention includes a medical device comprising a handle, a sheath extending from a proximal end of the handle, a retrieval basket, and a laser. In one embodiment, the sheath comprises a lumen and a distal end away from the proximal handle. The basket includes a plurality of legs and a tip at the distal end of the basket, the tip comprising two or more legs joined together. The basket and the sheath move relative to each other to achieve a collapsed position of the basket within the lumen of the sheath, and another position with the basket extending beyond the distal end of the sheath. The laser extends through the lumen of the sheath, and the laser and the sheath move relative to each other to achieve a first position with the laser within the lumen of the sheath and a second position with the laser extending beyond the distal end of the sheath. In one embodiment, the laser comprises at least one leg of the basket. According to a further embodiment, the laser and the legs move independent of the sheath. In another embodiment, the laser and the sheath move independent of the legs. In yet another embodiment, the laser moves independent of the sheath and the legs.

In a further embodiment, the medical retrieval device comprises a tubing comprising a tubing lumen. The tubing is slidably receivable in the lumen of the sheath, and the laser is axially positioned within the lumen of the tubing. The tubing comprises a pre-formed shape for exiting the distal end of the sheath at a predetermined angle.

In another embodiment, the proximal end of the handle comprises a knob mechanically coupled to the tubing wherein movement of the knob causes movement of the tubing. In one embodiment, the tubing moves longitudinally, and in an additional embodiment, the tubing moves rotationally. In another embodiment, the proximal end of the handle comprises a knob mechanically coupled to the laser wherein movement of the knob causes movement of the laser. In one embodiment, the laser moves longitudinally, and in an additional embodiment, the laser moves rotationally.

In another embodiment, the laser exits the distal end of the sheath at a predetermined angle. In one embodiment, the lumen of the sheath comprises a ramp. In yet another embodiment, the sheath comprises an adaptor at the proximal end of the sheath. The adaptor comprises a first opening and a lumen capable of receiving a laser and extending from the first opening to a second opening. The second opening is aligned with the at least one opening of the sheath.

According to a further aspect of the invention, a medical device includes a laser and a helical core element comprising a lumen. The helical core element is coupled to an elongated member. The elongated member extends from the helical core element to the proximal end of the device, and the helical core element comprises at least one opening. The laser extends through the lumen and exits the lumen through the at least one opening of the helical core element. In one embodiment, the at least one opening is shaped to direct the laser to exit the lumen at a predetermined angle.

According to another embodiment of the invention, a medical device includes a sheath having a lumen and an elongate member disposed within the lumen of the sheath. The elongate member is moveable relative to the sheath. The elongate member includes a retrieval assembly having a collapsed position within the lumen of the sheath and an expanded position when extended beyond a distal end of the sheath. The elongate member defines a lumen configured to receive a laser. The device further includes a handle having an actuation mechanism configured to assist in transitioning the retrieval assembly between the collapsed position and the expanding position. At least one of the elongate member or the sheath is connected to the actuation mechanism to provide relative movement between the elongate member and the sheath. The device further includes a laser, and the handle further includes a knob operatively connected to the laser to assist in manipulating the laser. The knob is configured to rotate the laser relative to the sheath and the elongate member. The knob is also configured to translate the laser longitudinally relative to the sheath and the elongate member. In some embodiments, the handle further includes an adaptor defining an adaptor lumen configured to receive the laser. The sheath defines an orifice aligned with the adaptor lumen and configured to receive the laser.

In some embodiments, the retrieval assembly includes a plurality of legs. At least one of the plurality of legs includes a free distal end. The at least one of the plurality of legs defines a portion of the lumen of the elongate member configured to receive a laser. The at least one of the plurality of legs comprises a preformed shape and exits the sheath at a predetermined angle. In some embodiments, the device also includes a laser disposed within the portion of the lumen of the at least one of the plurality of legs and moveable relative to the at least one of the plurality of legs. The laser exits the free distal end of the at least one of the plurality of legs to deliver energy to a material at a predetermined angle.

In other embodiments, the device includes a laser disposed within the lumen of the elongate member. The laser and the elongate member are moveable relative to each other. The laser comprises a preformed shape and exits the lumen of the elongate member at a predetermined angle. The elongate member defines an inner surface angled relative to a longitudinal axis of the elongate member to direct the laser at a predetermined angle relative to the longitudinal axis of the elongate member. The predetermined angle is between approximately 20 degrees and approximately 60 degrees relative to the longitudinal axis of the elongate member. The laser includes a laser cannula. In some embodiments, each of the plurality of legs is joined at a distal tip of the retrieval assembly.

In further embodiments of the device, the retrieval assembly comprises a helical element having a lumen and at least one opening configured to permit the laser to exit the lumen of the helical element. The elongate member and the helical element are formed from the same piece of material, and the lumen of the elongate member is in communication with the lumen of the helical element. In such embodiments, the laser includes a laser cannula. The at least one opening is configured to direct the laser to exit the lumen of the helical element at a predetermined angle.

In other embodiments, the retrieval assembly comprises a grasping assembly including a plurality of legs each having a free distal end. The grasping assembly is formed by removing at least a portion of the elongate member. At least a portion of the elongate member proximal to the plurality of legs is removed to increase the flexibility of the device. At least one of the plurality of legs includes a textured surface to assist in gripping a material. The textured surface includes teeth on an inner surface of the at least one of the plurality of legs. In some embodiments, the device further includes a laser disposed within the lumen of the elongate member and moveable relative to the elongate member.

In still further embodiments, a medical device includes a sheath having a lumen, an opening on a side of the sheath at a distal end of the sheath, and an inner surface proximate the opening to direct a laser through the opening. The device further includes an elongate member disposed within the lumen of sheath and moveable relative to the sheath. The elongate member includes a retrieval assembly having a collapsed position within the lumen of the sheath and an expanded position when extended beyond the distal end of the sheath. The retrieval assembly includes a first leg, a second leg, and a tip joining the first and second legs together. The inner surface is angled relative to a longitudinal axis of the sheath. A laser is disposed within the lumen of the sheath. A ramp-like structure defines the inner surface. The ramp-like structure is configured to direct the laser at an angle between approximately 20 degrees and approximately 60 degrees relative to a longitudinal axis of the sheath. At least a portion of the elongate member is disposed within a passage of the ramp-like structure, and the elongate member is movable relative to the ramp-like structure.

In some embodiments, the laser is disposed within a laser cannula and is moveable relative to the laser cannula. In such embodiments, the inner surface is positioned to direct the laser cannula to exit the lumen of the sheath through the opening at a predetermined angle relative to a longitudinal axis of the sheath.

In further embodiments of the invention, a method of performing laser lithotripsy on a material includes providing a medical device comprising a sheath, an elongate member disposed within a lumen of the sheath, and a laser at least partially disposed within a lumen of the elongate member, the elongate member including a retrieval assembly at a distal end of the elongate member. The method further includes transitioning the retrieval assembly from a collapsed position within the lumen of the sheath to an expanded position, capturing the material within the retrieval assembly, and positioning the laser to direct energy toward the material. The method also includes reducing the size of the captured material with the laser and removing the medical device.

In some embodiments of the above method, transitioning the retrieval assembly from the collapsed position to the expanded position includes moving the elongate member relative to the sheath. Positioning the laser includes rotating the laser relative to the elongate member. Positioning the laser also includes moving the laser longitudinally relative to the elongate member. In some embodiments, the retrieval assembly includes a plurality of legs. At least one of the plurality of legs includes a free distal end and defines a portion of the lumen of the elongate member. The at least one of the plurality of legs comprises a preformed shape and exits the sheath at a predetermined angle. In such an embodiment, positioning the laser includes extending the laser through the portion of the lumen of the at least one of the plurality of legs. Positioning the laser also includes extending the laser beyond the free distal end of the at least one of the plurality of legs.

In some embodiments of the method, the laser comprises a pre-formed shape and exits the lumen of the elongate member to direct energy toward the material at a predetermined angle. In other embodiments, positioning the laser includes extending the laser against an inner surface of the elongate member angled relative to a longitudinal axis of the elongate member. The inner surface has an angle between approximately 20 degrees and approximately 60 degrees relative to the longitudinal axis of the elongate member. In further embodiments, the laser includes a laser cannula.

In still further embodiments of the above method, the retrieval assembly comprises a helical element having a lumen and at least one opening, and positioning the laser includes extending the laser through the lumen of the elongate member, through the lumen of the helical element, and through the at least one opening of the helical element. The elongate member and the helical element are formed from the same piece of material, and the lumen of the elongate member is in communication with the lumen of the helical element. The laser includes a laser cannula. At least one opening is configured to direct the laser to exit the lumen of the helical element at a predetermined angle.

In a further embodiment of the above method, the retrieval assembly comprises a grasping assembly including a plurality of legs each having a free distal end. The grasping assembly is formed by removing at least a portion of the elongate member. At least a portion of the elongate member proximal to the plurality of legs is removed to increase the flexibility of the device. At least one of the plurality of legs includes a textured surface to assist in gripping a material. The textured surface includes teeth on an inner surface of the at least one of the plurality of legs. In some embodiments, capturing the material further includes gripping the material with the plurality of legs and positioning the laser includes extending the laser relative to the elongate member, beyond the lumen of the elongate member, and proximate the material.

In yet another embodiment of the invention, a method of performing laser lithotripsy on a material includes providing a medical device having a sheath including a lumen, an opening on a side of the sheath at a distal end of the sheath, and an inner surface proximate the opening to direct a laser through the opening. The medical device also includes an elongate member disposed within the lumen of sheath and moveable relative to the sheath, the elongate member including a retrieval assembly. The medical device further includes a laser disposed within the lumen of the sheath. The method also includes transitioning the retrieval assembly from a collapsed position within the lumen of the sheath to an expanded position, capturing the material within the retrieval assembly, and positioning the laser to direct energy toward the material. The method further includes reducing the size of the captured material with the laser and removing the medical device.

In some embodiments, the inner surface includes an angle between approximately 20 degrees and approximately 60 degrees relative to a longitudinal axis of the sheath. In such embodiments, positioning the laser includes directing a portion of the laser along the inner surface. Positioning the laser further includes extending a portion of the laser through the opening of the sheath.

In further embodiments, a ramp-like structure defines the inner surface. At least a portion of the elongate member is disposed within a passage of the ramp-like structure and the elongate member is movable relative to the ramp-like structure.

Both the foregoing general description and the following detailed description are exemplary and explanatory only, and are not restrictive of the invention as claimed.

BRIEF DESCRIPTION OF THE DRAWINGS

Exemplary embodiments of the invention are illustrated in the accompanying drawings. Wherever possible, the same reference numbers will be used throughout the drawings to refer to the same or like parts. The drawings are not necessarily to scale. Emphasis is instead generally being placed upon illustrating the principles of the invention.

FIG. 1 is a side plan view of a medical retrieval device including a medical retrieval basket assembly in a fully-extended or open position according to an illustrative embodiment of the invention.

FIG. 2 is a side plan view of the device depicted in FIG. 1 including the retrieval basket assembly in a collapsed/retracted position according to an illustrative embodiment of the invention.

DETAILED DESCRIPTION

Figure 3A:
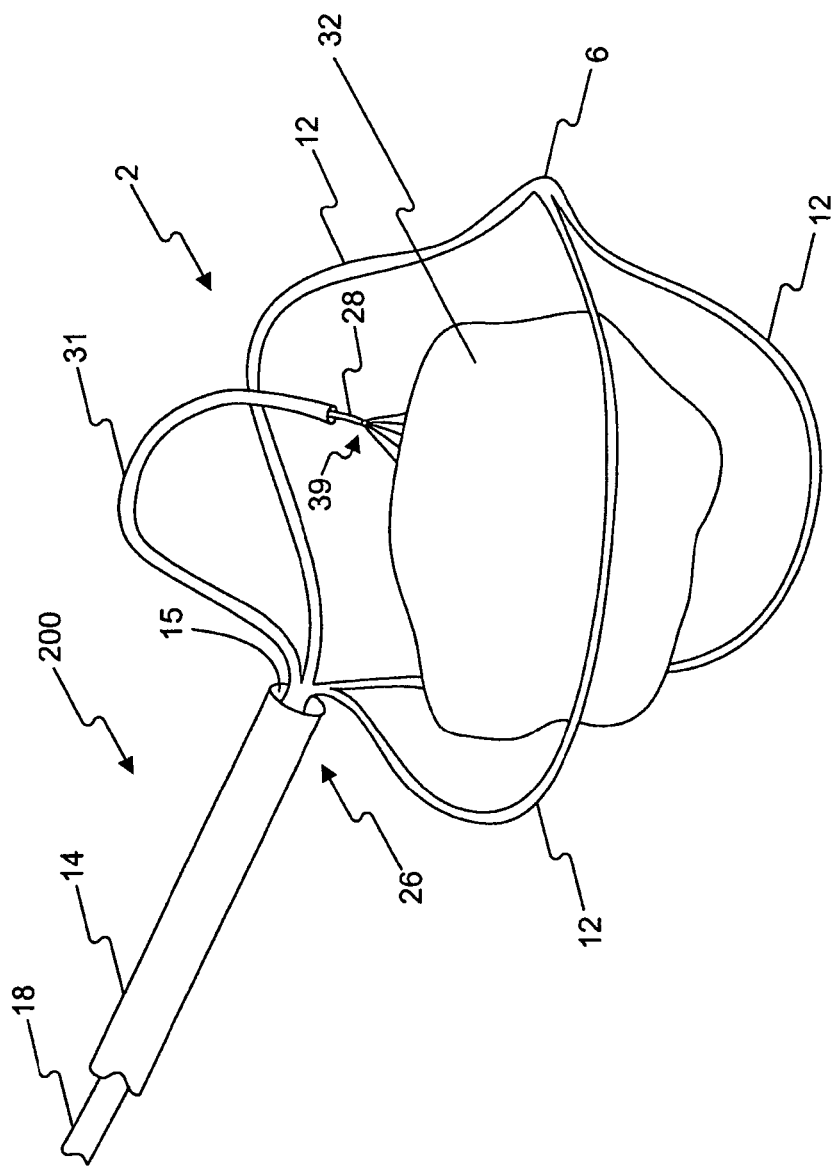
FIG. 3a is an illustrative view of a portion of a retrieval device including a basket having four legs and a laser according to an illustrative embodiment of the invention.

Exemplary embodiments of the present invention generally provide for medical retrieval devices comprising a laser for breaking up or fragmenting material to be captured by the device and removed from within the body of a patient. According to the embodiments of the invention described herein, the reference "proximal" generally refers to the end of the device closer to the user and the term "distal" generally refers to the end of the device closer to the patient. The "material" to be captured, fragmented, or otherwise acted on by the device may be, for example, a stone or other bodily tissue or foreign object within the body of a patient. The stone may be, for example, a kidney stone, a struvite, a uric acid stone, a cystine stone, a ureteral stone, a urinary bladder stone, a gall bladder stone, a stone within the biliary tree, or any other solid deposit commonly removed from a body structure or passageway within the body. For instance, a stone may also be a tumor or a polyp. Stones may contain various combinations of chemicals including, but not limited to, calcium, oxalate, and phosphate. The stone may be of any size, and could have a length or diameter of approximately 1 mm to 12 mm. It is understood that these lengths and diameters are merely exemplary and that aspects of the invention may assist in the removal of stones or other bodily tissue or foreign objects larger or smaller than those discussed herein. Stones may be of any shape and could be, for example, flat, round, smooth, or jagged.

The devices of the invention may assist in the immobilization and removal of stones that are both impacted and free floating. Each of the devices described herein may include a retrieval assembly to assist in capturing and removing material from the body. The retrieval assemblies may be made from any laser resistant material or combination of laser resistant materials, including materials having a highly reflective surface such as, for example, nitinol, titanium, and cobalt chromium, and materials comprising laser energy absorbing plastics, such as, for example, PTFE. The retrieval assemblies may include a retrieval basket, a grasping assembly, or a stone cone. In addition, although not shown in all of the exemplary figures, each of the devices described herein may also include a sheath and a handle. Such sheaths and handles of the invention will be described in greater detail below. Each of the devices described herein may further include a laser for fragmenting or breaking up the material prior to removal of the material from the body.

FIG. 1 illustrates a medical retrieval device 100 according to an exemplary embodiment of the invention. Such a device 100 may include a handle 16 having a proximal end 44 and a distal end 46, a sheath 14, and a retrieval assembly, such as a basket 2. The handle 16, the sheath 14, and the basket 2 of FIG. 1 are not shown in their correct size or proportion to each other. The sheath 14 typically may be much longer than the handle 16 or the basket 2 to allow insertion into a body cavity, canal, or tract. The basket 2 may be made of resilient material, such as metal wires, forming two or more basket legs 12. The basket 2 features a proximal end portion 24, a distal end portion 22, and a distal tip 6. Although the following illustrative embodiments and corresponding figures depict a retrieval basket 2 having a certain number of legs 12, this depiction is for illustrative purposes only, and each of the retrieval baskets 2 in the following embodiments are not limited to the number of legs 12 illustrated. The legs 12 may be made from any of the materials listed above or any combination thereof. The basket 2 may be the type that is collapsed within the sheath 14 for entry into the body.

The sheath 14 may be formed from any suitable biocompatible material known in the art. Such materials may include, but are not limited to, stainless steel alloys (such as 300 and 400 series), cobalt chromium, nickel, titanium, nitinol, thermoforming plastic, polytetrafluoroethylene ("PTFE"), and expanded polytetrafluoroethylene ("EPTFE"). The sheath 14 may also be a metal coated with a polymer.

The overall length and diameter of the sheath 14 may vary depending on the application. For example, a relatively long sheath 14 may be advantageous for retrieving stones or other calculi deep within the body of the patient. In each embodiment, the sheath 14 may extend from the handle 16 to a distal sheath end 26. In addition, a sheath 14 having a relatively small diameter may be advantageous for retrieving stones from restricted passageways within the human urinary tract. The sheath 14 may include at least one open lumen or channel 15 and may be sized to accept the legs 12 of the basket 2, thereby collapsing the basket 2 (FIG. 2). As will be described below, the sheath 14 may be fixedly or operatively connected to a portion of the handle 16 depending on the desired operating characteristics of the devices of the present embodiment. For example, in some embodiments, the sheath 14 may be moveable relative to the basket 2 to expand or collapse the basket 2.

An elongate member 18 such as a cable, coil, shaft, guidewire, or mandril wire may extend within the lumen 15 from an actuation mechanism 4 in the handle 16 to a base 13 of the basket where the elongate member 18 is coupled to the basket base 13. This coupling may be facilitated by any conventional coupling means known in the art. Operation of the actuation mechanism 4 by an operator may cause the basket 2 to move relative to the sheath 14 between a collapsed position within the sheath 14 as illustrated in FIG. 2, to an expanded position outside of the sheath 14 where the basket 2 may be open and extended beyond the distal end of the sheath 26 as shown in FIG. 1.

Alternatively, the actuation mechanism 4 may be operatively joined to the sheath 14. In such an embodiment, the actuation mechanism 4 may enable a user to advance the sheath 14 over the stationary basket 2 and elongate member 18 to thereby collapse the basket 2 within the lumen 15 of the sheath 14. The actuation mechanism 4 may also slide the movable sheath 14 in the proximal direction to expose the stationary basket 2 and allow it to expand. Alternatively, a second actuation mechanism (not shown) may be joined to the elongate member 18 such that the sheath 14 and the basket 2 may be actuated independently. In general, these types of basket/sheath movement configurations and related handle mechanisms may be seen in existing product designs available from, for example, Boston Scientific Corporation (Natick, Mass.).

With the basket 2 restrained and collapsed within the sheath 14 as shown in FIG. 2, the sheath 14 may be inserted into the body by an operator to a treatment site in the body. As used herein, the term "treatment site" means a location within the body of a patient where material to be retrieved may be located (e.g., a stone in the urinary tract). By placing the basket 2 in its unrestrained open/expanded position, as illustrated in FIG. 1, the basket 2 may, for example, dilate the body tract in which it has been placed and/or may be manipulated by the operator to entrap or capture material within the basket 2. The basket 2 and/or the sheath 14 may then be moved to cause the legs 12 of the basket 2 to close around the material and capture it. According to one embodiment, the material may first be captured and then broken down and/or fragmented by, for example, a laser or other lithotripsy device (not shown). In such an embodiment, the material may also be crushed or otherwise broken down and/or fragmented by the basket 2 after capture. Alternatively, the material may first be broken down and/or fragmented by a laser before being captured by the basket 2. The material may be withdrawn from the body along with the sheath 14 and the basket 2 that may be holding the material.

Figure 3B:
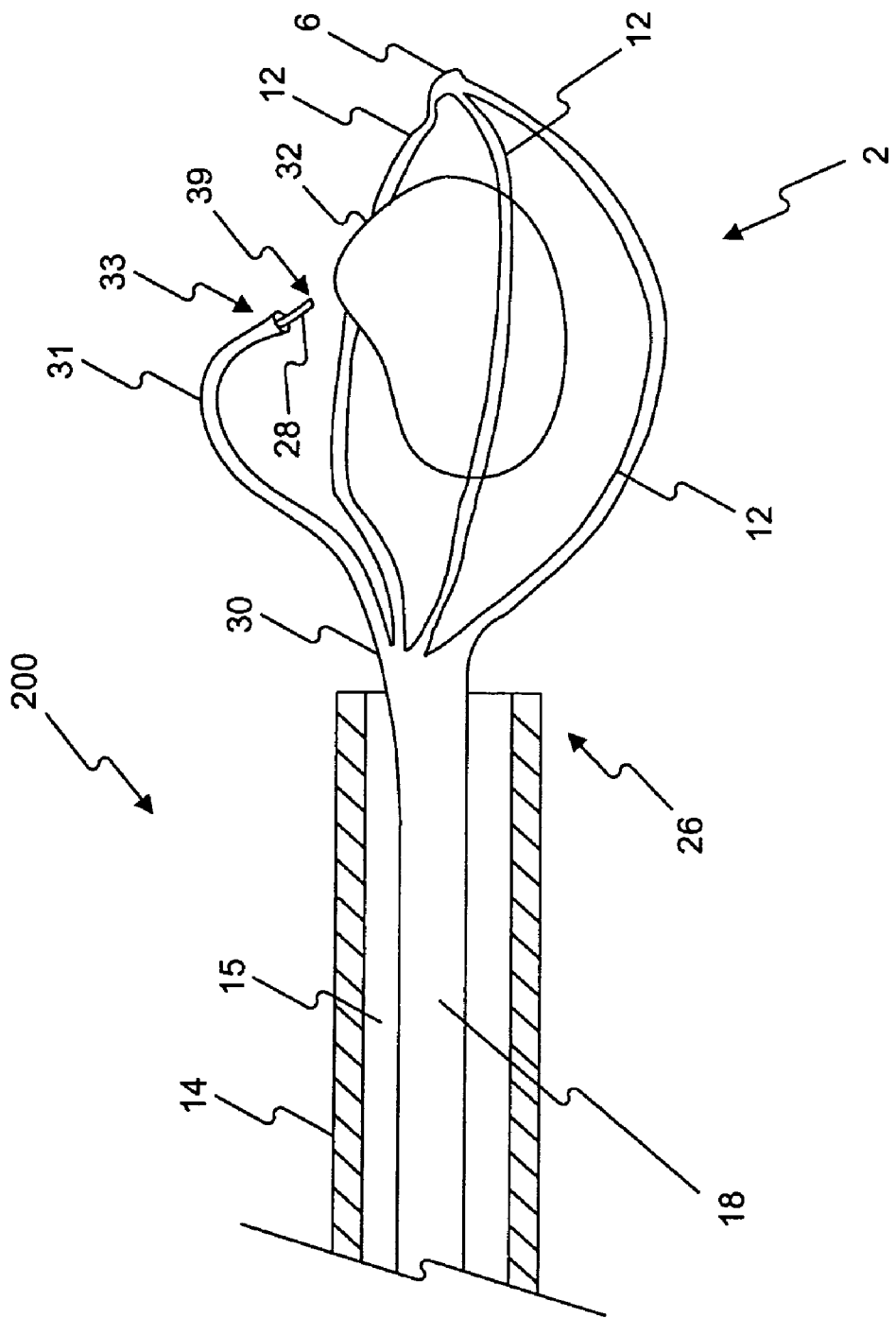
FIG. 3b is a side plan view of the basket depicted in FIG. 3a with the retrieval basket assembly in a fully-extended or open position.

FIG. 3a is an illustrative view of a portion of a retrieval device 200 including a basket 2 having four legs 12 and a laser 28 according to an illustrative embodiment of the invention. FIG. 3b is a side plan view of the basket 2 depicted in FIG. 3a with the retrieval basket assembly 2 in a fully-extended or open position. As shown in FIG. 3, the device 200 may include an elongate member 18, and a retrieval basket 2 having a distal tip 6 and four legs 12, 31. The device 200 may also include a sheath 14 having a lumen 15 and a distal sheath end 26. A hollow laser cannula 30 may extend through the sheath 14 and may form the fourth leg 31 of the basket 2 when the basket 2 is in an open position. The laser cannula 30 may be formed of at least part of the elongate member 18 of the device 200. Alternatively, the laser cannula 30 may be formed from a separate piece of material and connected to at least a portion of the elongate member 18 so as to form part of the basket 2. Three of the four legs 12 of the basket 2 may be joined at the distal tip 6. The fourth leg 31 may include a free distal end 33 that may not be joined to any other structure of the basket 2.

According to the embodiment shown in FIG. 3, a laser 28 may be passed through the hollow laser cannula 30. A laser tip 39 may exit a distal end 33 of the fourth leg 31 and energy from the laser 28 may be directed towards material 32 within the body at a predetermined angle. In another embodiment, the laser 28 may not be disposed within the laser cannula 30, rather, the laser 28 may extend through the lumen 15 of the sheath 14 and may exit the sheath 14 at the sheath distal end 26 when the basket 2 is in an open position. In one embodiment, the laser cannula 30 and/or the laser 28 may exit the sheath 14 along with the legs 12 of the basket 2 when the basket 2 is placed in an open position. In another embodiment, the laser cannula 30 and/or laser 28 may be moveable independent from the legs 12 of the basket 2 and/or the elongate member 18. In such an embodiment, the laser cannula 30 and/or the laser 28 may exit the sheath 14 separately from the legs 12 of the basket 2 when the basket 2 is placed in an open position.

In one embodiment, the laser cannula 30 may be preformed at a predetermined angle and shape. Thus, the laser 28 may direct laser energy toward material 32 captured within the basket 2 depending on the shape of the laser cannula 30. In another embodiment, the laser 28 itself may be preformed to exit the sheath 14 at a predetermined angle. The desired shape of the laser cannula 30 and/or laser 28, and the resulting angle at which the energy from the laser 28 is applied will depend on, for example, the type of procedure performed, the size of the material 32, the composition of the material 32, and/or the location of the material 32 within the body. In each of the device embodiments discussed herein including a laser cannula 30 and/or a laser 28 having a predetermined angle, the shape of the laser cannula 30 and/or the laser 28 may be such that the captured material 32 may be forced into the basket 2 of the device when laser energy is directed toward the material 32.

Figure 4A:
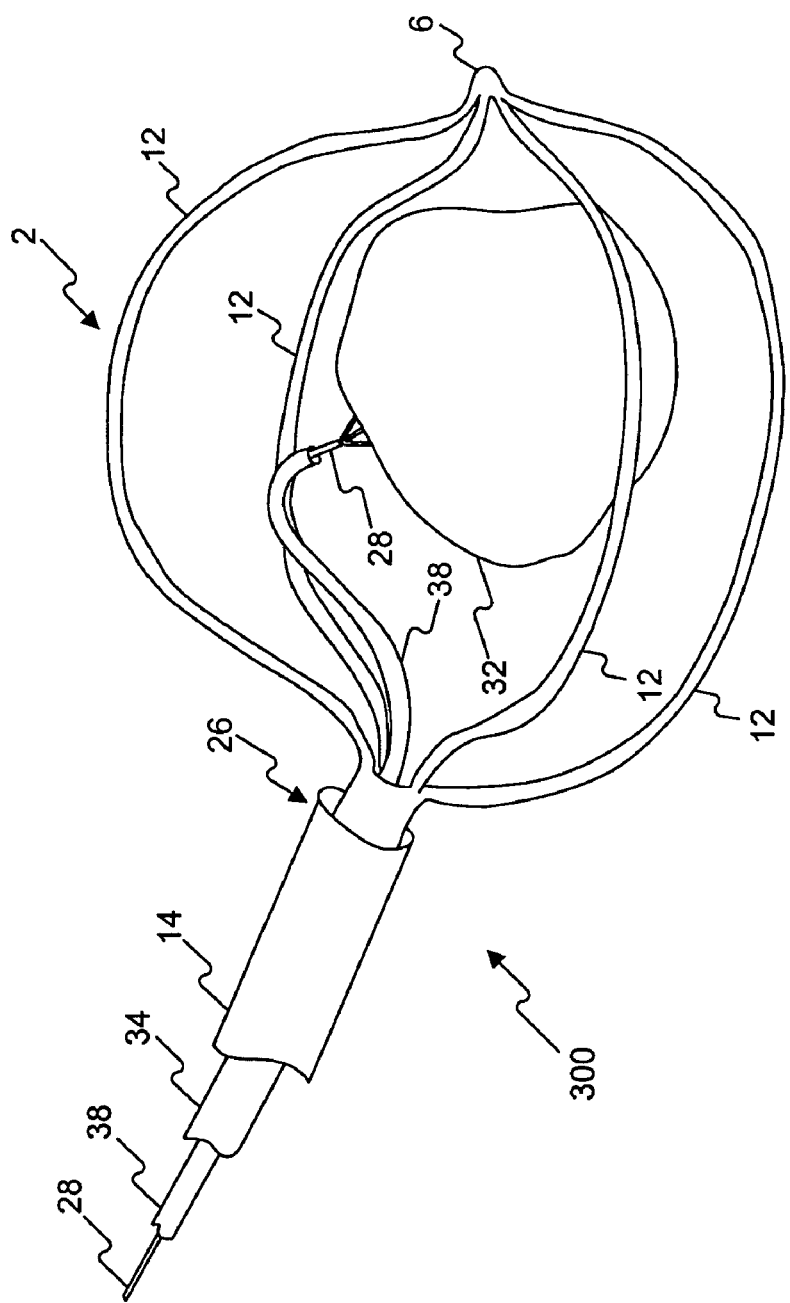
FIG. 4a is an illustrative view of a portion of a retrieval device including a basket having four legs and a laser according to an illustrative embodiment of the invention.
Figure 4B:
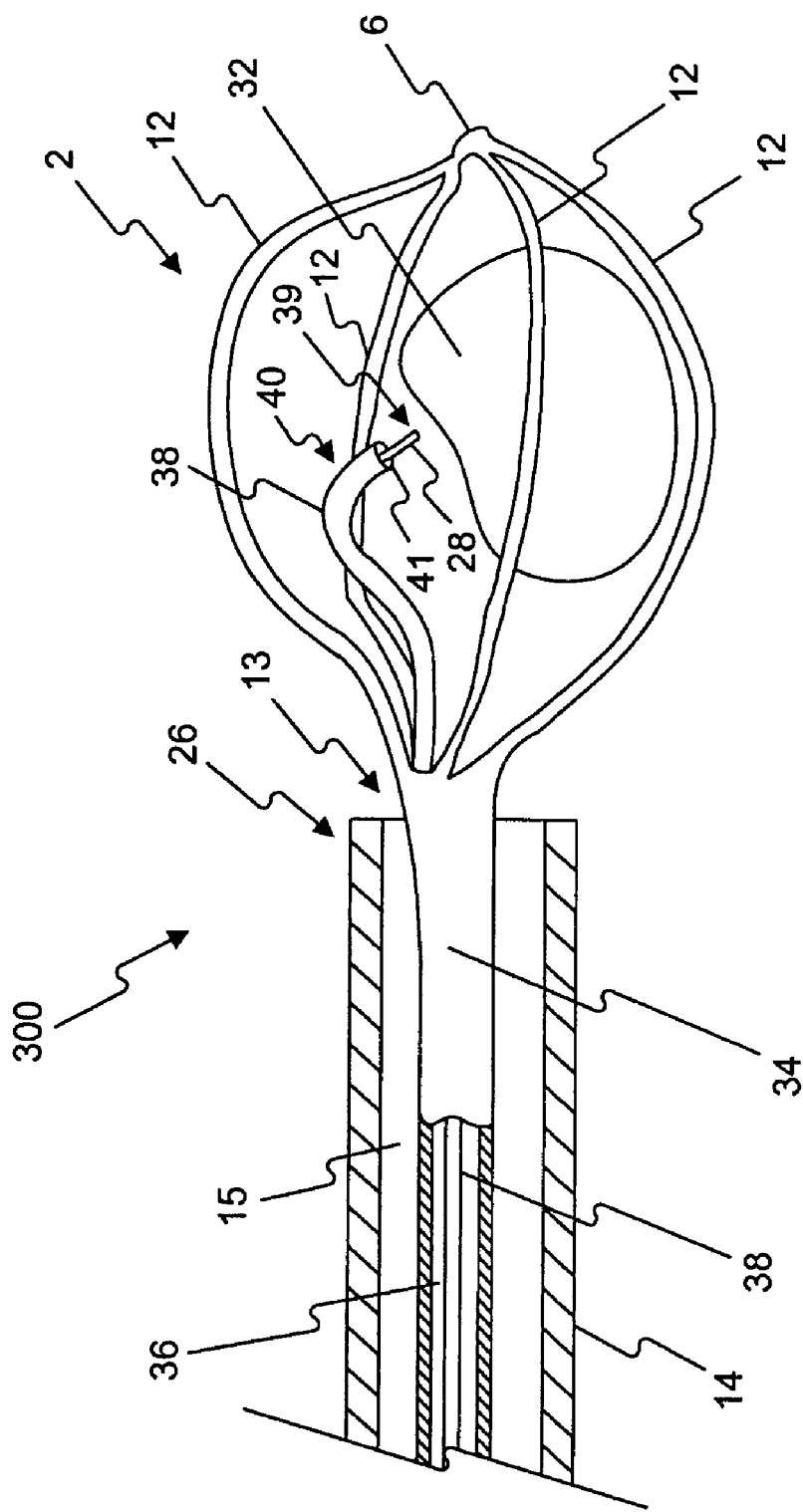
FIG. 4b is a side plan view of the basket depicted in FIG. 4a with the retrieval basket assembly in a fully-extended or open position.

FIG. 4a is an illustrative view of the retrieval device 300 including a retrieval basket 2 comprising four legs 12 and a laser 28 according to an illustrative embodiment of the invention. FIG. 4b depicts a side plan view of the retrieval basket 2 in FIG. 4a in a fully-extended or open position. As shown in FIG. 4b, at least a portion of the device 300 may be constructed from a single piece of hollow cannula 34 defining a lumen 36. A portion of the cannula 34 may be cut, etched, or otherwise removed to define four legs 12 of a retrieval basket 2. The hollow cannula 34 may extend within a lumen 15 of a sheath 14 and may exit a sheath distal end 26 when the retrieval basket 2 is in an open and/or fully extended position. The device 300 may further include a hollow piece of tubing 38 defining at least one lumen 41 and a laser 28 may be inserted through the lumen 41 of the tubing 38. The tubing 38 may have a smaller outer diameter than a diameter of the lumen 36 of the cannula 34, and the tubing 38 carrying the laser 28 may exit the lumen 36 at the base 13 of the basket 2. A laser tip 39 may exit the tubing 38 at a tubing distal end 40 and energy from the laser 28 may be directed towards material 32 within the basket 2. According to one embodiment, the tubing 38 may be pre-formed to direct the energy of laser 28 towards the material 32 at a predetermined angle. Alternatively, the laser 28 itself may be pre-formed to exit the base 13 of the basket 2 at a predetermined angle.

Figure 4C:
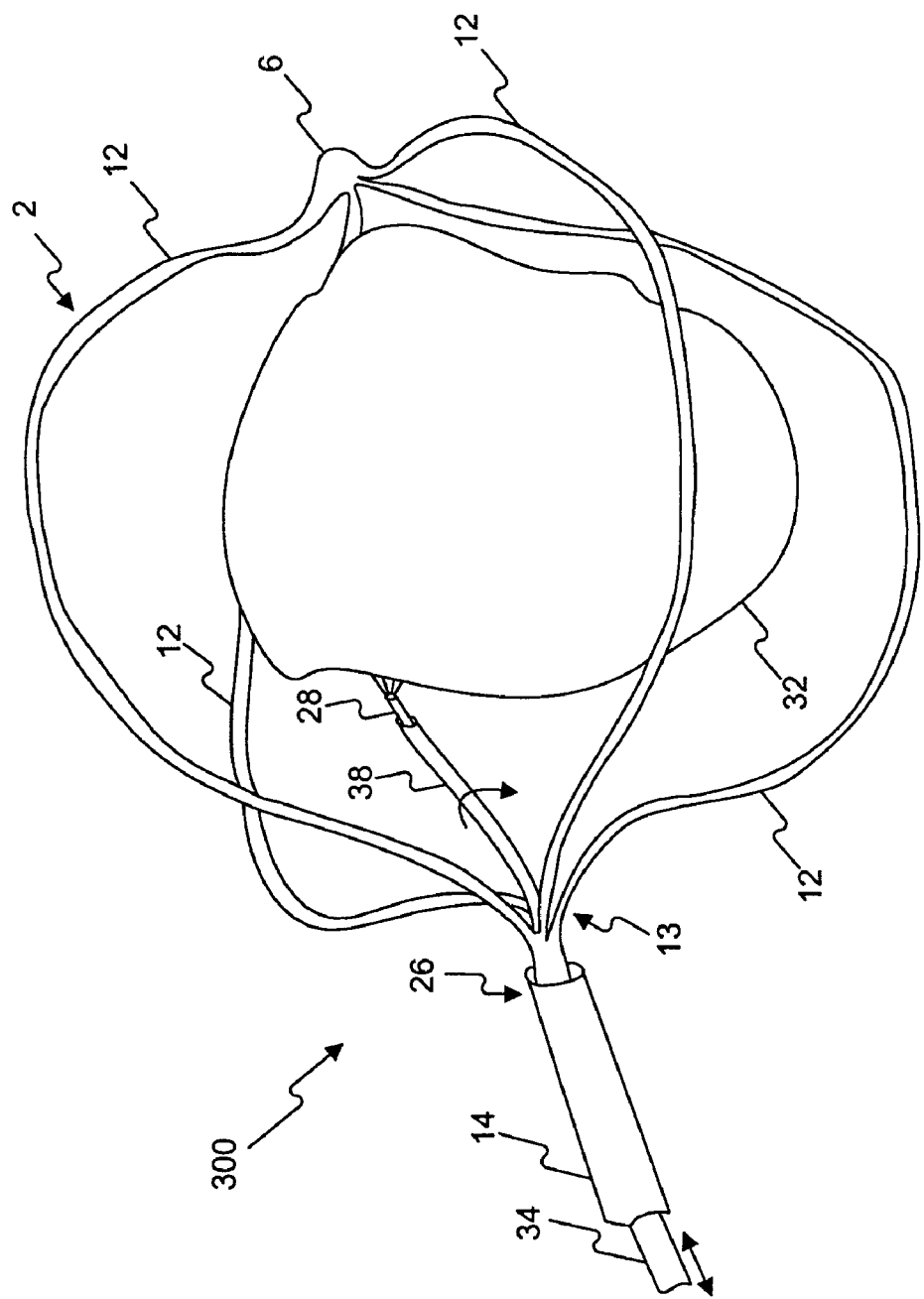
FIG. 4c is an illustrative view of a portion of a retrieval device including a basket having four legs and a laser according to an illustrative embodiment of the invention.
Figure 4D:
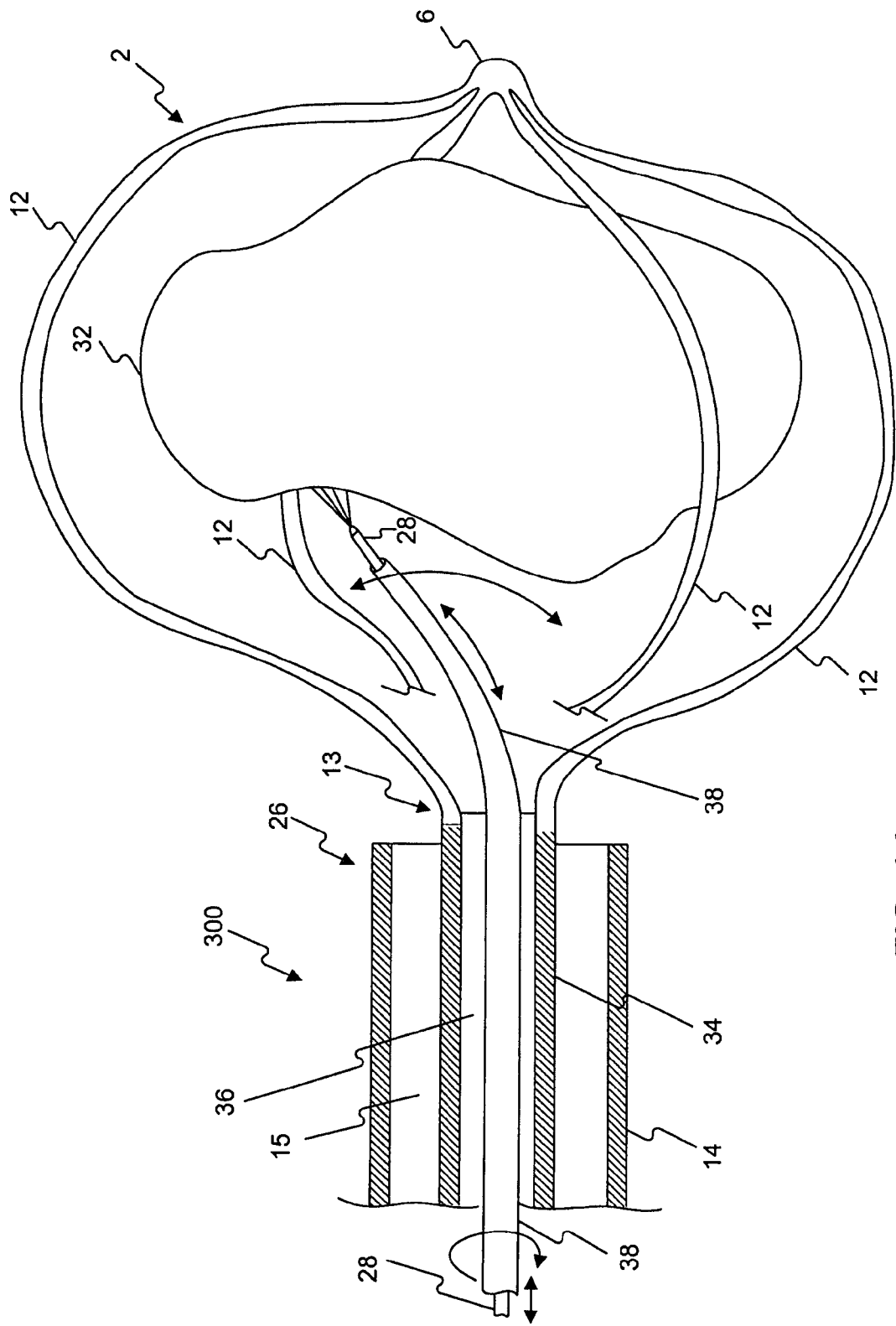
FIG. 4d is a side plan view of the basket depicted in FIG. 4c with the retrieval basket assembly in a fully-extended or open position.

FIG. 4c is an illustrative view of a portion of the retrieval device 300 including a basket 2 having four legs 12 and a laser 28 according to an illustrative embodiment of the invention. FIG. 4d is a side plan view of the basket 2 depicted in FIG. 4c with the retrieval basket assembly 2 in a fully-extended or open position. As shown in FIG. 4d, the laser 28 is inserted through the lumen 41 of the tubing 38 and the laser tip 39 exits the tubing 38 at the tubing distal end 40. In other embodiments, the laser 28 is free from any tubing 38. The laser 28 and/or tubing 38 carrying the laser 28 may be fixedly attached, or otherwise stationary relative to the cannula 34 so as to deploy with the legs 12 of the basket 2 as the basket 2 exits the sheath 14. Alternatively, the laser 28 and/or tubing 38 carrying the laser 28 may be independent from the legs 12 of the basket 2 and may be deployed and/or otherwise manipulated separately from the legs 12. As such, the laser 28 itself, without the tubing 38, may be passed through the hollow cannula 34 and may exit the lumen 36 of the cannula 34 at the base 13 of the basket 2. In such embodiments, the laser 28 and/or tubing 38 carrying the laser 28 may be rotated 360 degrees coaxially within the lumen 36 of the cannula 34, allowing the laser 28 to direct laser energy at several different points on the material 32. Thus, the laser 28 and/or tubing 38 carrying the laser 28 may also be slid laterally out through the base 13 of the basket 2 and may be pulled back into and through the sheath 14. According to one embodiment, the laser 28 and/or tubing 38 carrying the laser 28 may be pre-formed to allow the laser's 28 energy to be directed towards the material 32 at a predetermined angle. In another embodiment, the laser 28 and/or tubing 38 carrying the laser 28 is preformed such that sliding the laser 28 and/or tubing 38 carrying the laser 28 in a lateral direction alters the angle at which the laser 28 directs its energy towards the material 32. In one embodiment, sliding the laser 28 and/or tubing 38 carrying the laser 28 towards the distal tip 6 of the basket 2 causes an increase in the angle at which the laser 28 directs its energy at the material 32.

Figure 5:
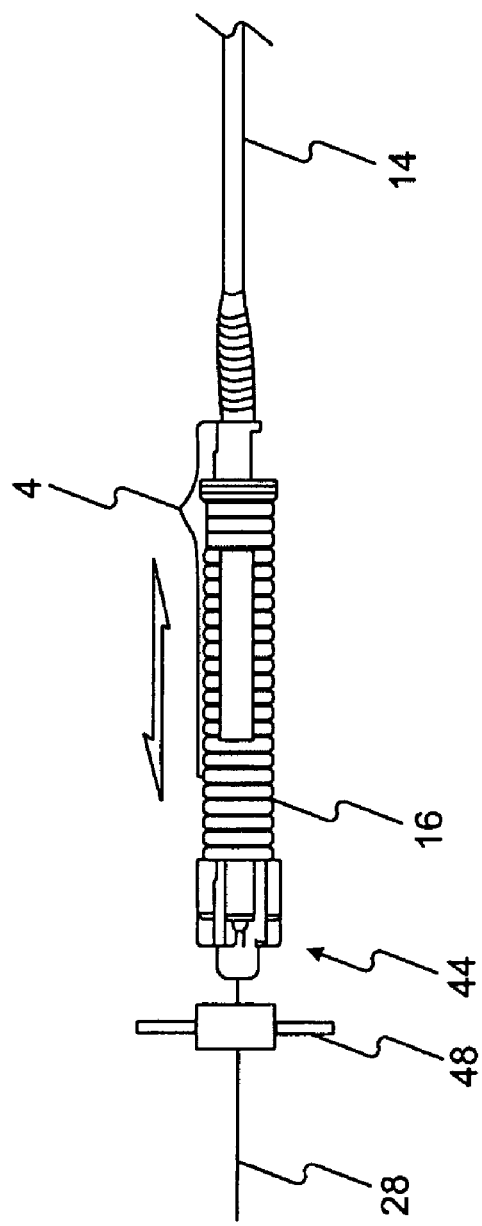
FIG. 5 is an illustrative view of a handle of a medical retrieval device according to an illustrative embodiment of the invention.
Figure 6:
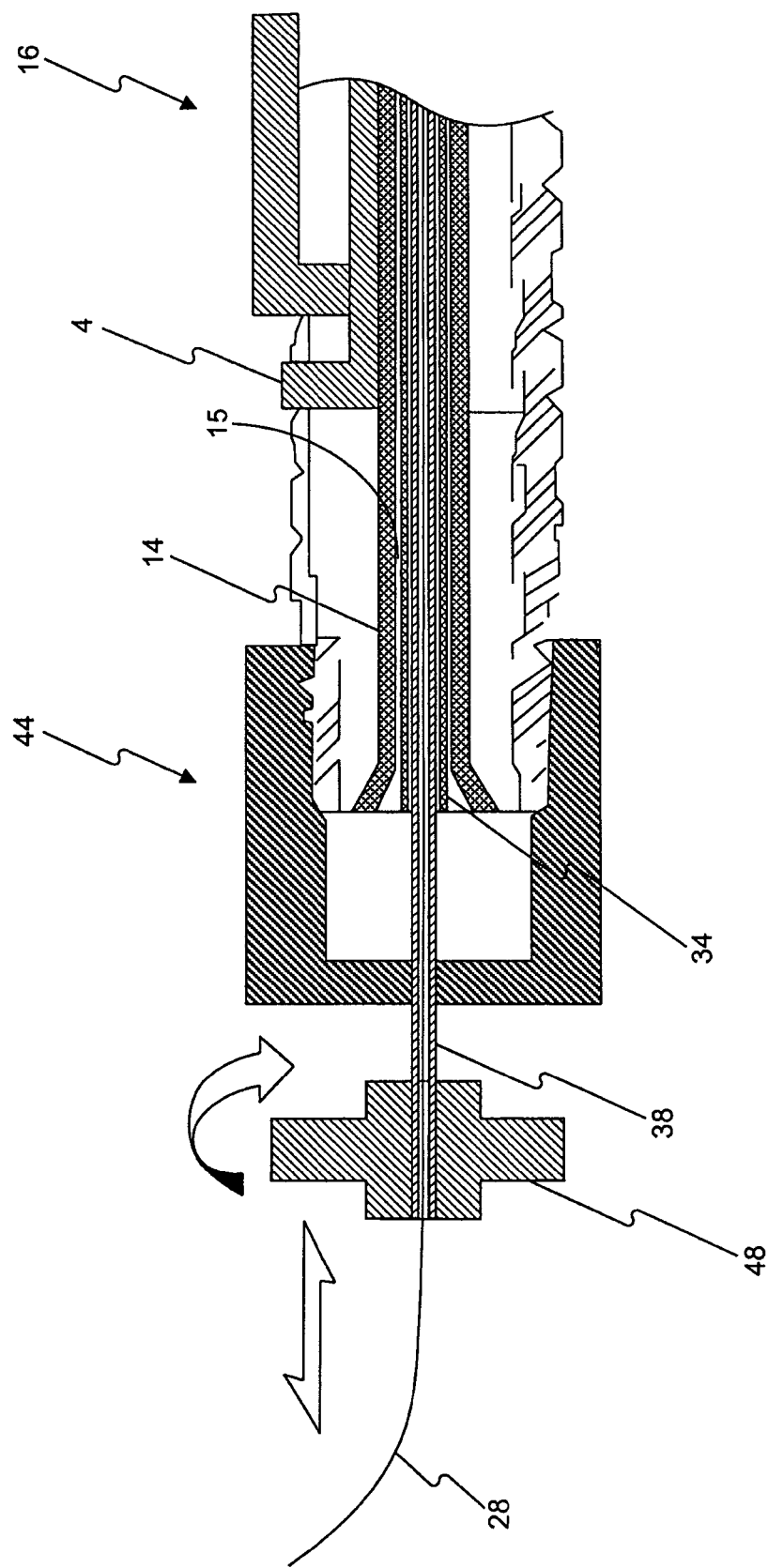
FIG. 6 is an exploded side plan view of a proximal end of a handle of a medical retrieval device comprising a laser according to an illustrative embodiment of the invention.

FIG. 5 depicts the handle 16 of the retrieval device according to one embodiment of the invention. FIG. 6 depicts an exploded view of the proximal end 44 of the handle 16 shown in FIG. 5. Each of the device embodiments described herein can include a handle 16 according to the following illustrative embodiments. As shown in FIG. 6, the laser 28 and/or tubing 38 carrying the laser 28 may extend through a proximal end 44 of the handle 16, allowing a user to pass the laser 28 and/or tubing 38 carrying the laser through the handle 16 and to position the laser 28 as desired. In one embodiment, the laser 28 and/or the tubing 38 carrying the laser 28 may be mechanically coupled to a knob 48 such that turning the knob 48 in a clockwise or counterclockwise position causes the laser 28 and/or tubing 38 carrying the laser 28 to rotate in a corresponding clockwise or counterclockwise direction. Additionally, the laser 28 and/or tubing 38 carrying the laser 28 may be mechanically coupled to the knob 48 such that laterally sliding the knob 48 causes the laser 28 and/or tubing 38 carrying the laser 28 to move in a corresponding lateral direction. Such movements are illustrated by the arrows shown in FIG. 6. In an additional embodiment, laterally sliding the knob 48 may cause a change in the angle at which the laser 28 exits the sheath 14 and directs its energy towards the material 32.

As shown in FIG. 6, a portion of the sheath 14 and a portion of the cannula 34 may extend through a portion of the handle 16. The sheath 14 may be coupled to a portion of the handle 16 by any coupling means known in the art such as, for example, crimping or adhesives. For example, in some embodiments, the sheath 14 may be coupled to an actuation mechanism 4 of the handle 16 such that manipulation of the actuation mechanism 4 causes a corresponding movement of the sheath 14. Moving the actuation mechanism 4 in a distal direction may move the sheath over an expanded basket 2, thereby collapsing the basket 2 within the sheath 14 while moving the actuation mechanism 4 in a proximal direction may retract the sheath 14 and allow the basket 2 to expand. In such an embodiment, the cannula 34 may be stationary relative to the handle 16 and may be fixedly coupled thereto by any conventional means.

In other embodiments, the cannula 34 may be moveable relative to the sheath 14. In such embodiments, the sheath 14 may be coupled to a portion of the handle 16 by, for example, crimping, adhesives, or any other coupling means known in the art. For example, the cannula 34 may be coupled to the actuation mechanism 4 such that actuation of the actuation mechanism 4 may cause a corresponding movement of the cannula 34. As shown in FIG. 6, and as described above, the tubing 38 carrying the laser 28 may be disposed within a lumen 36 of the cannula 34 and may pass through the handle 16. The tubing 38 may exit the proximal end 44 of the handle 16 and may be moveable relative to the sheath 14 and/or the cannula 34. The tubing 38 may also be moveable relative to the handle 16.

According to a further embodiment, the laser 28 and/or tubing 38 carrying the laser 28 may be mechanically coupled to the sheath 14 such that turning the sheath 14 in a clockwise or counterclockwise position causes the laser 28 and/or tubing 38 carrying the laser 28 to rotate in a corresponding clockwise or counterclockwise direction. In an alternate embodiment, the laser 28 and/or tubing 38 carrying the laser 28 may be mechanically coupled to the sheath 14 and the sheath 14 may be mechanically coupled to the knob 48 such that turning the knob 48 in a clockwise or counterclockwise position may cause both the sheath 14 and the laser 28 and/or the tubing 38 carrying the laser 28 to rotate in a corresponding clockwise or counterclockwise direction.

Figure 7:
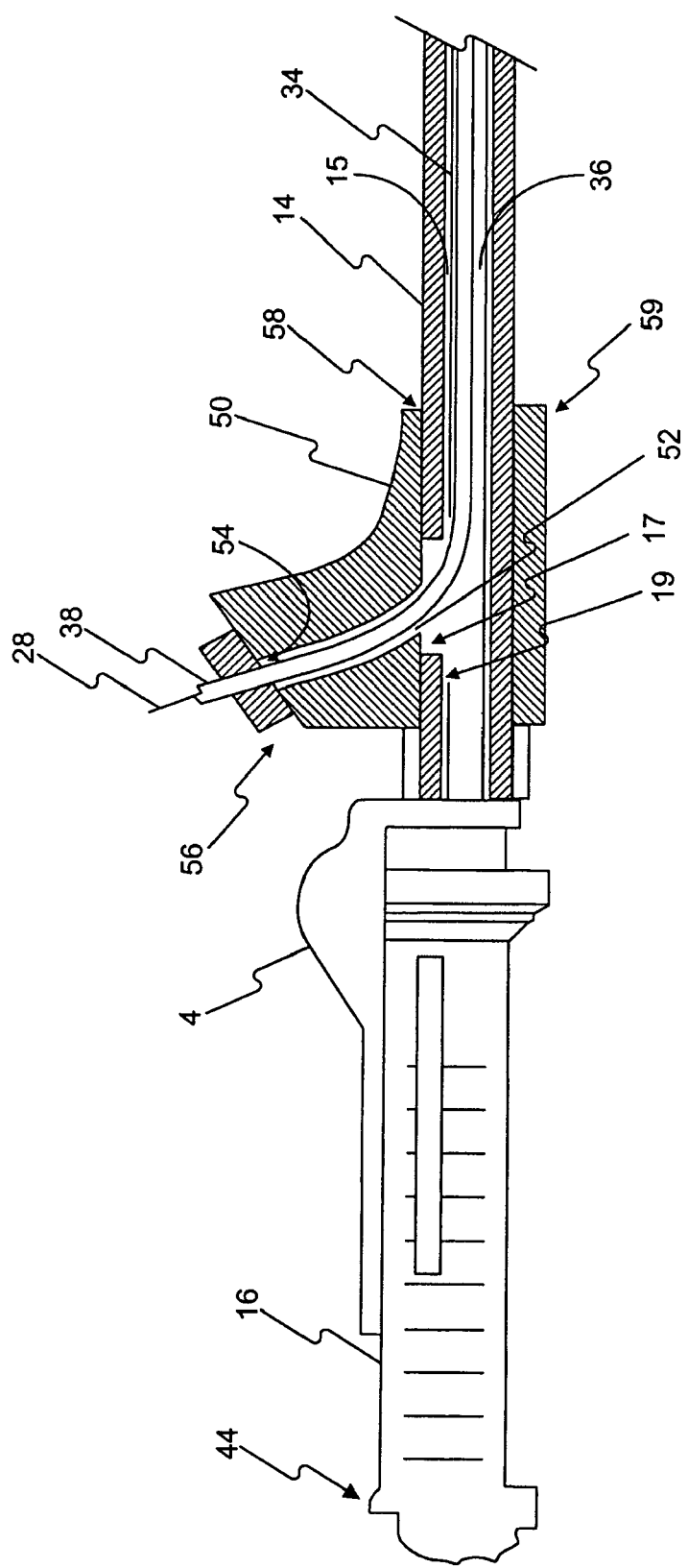
FIG. 7 is a illustrative view of a portion of a medical retrieval device including an adaptor for receiving a laser according to an illustrative embodiment of the invention.

In each of the device embodiments described herein, the handle 16 may include an adaptor 50. As illustrated in FIG. 7, the adaptor may include a lumen 52 extending from a first opening 54 at the proximal end 56 of the adaptor to a second opening 58 at a distal end 59 of the adaptor 50. In one embodiment, the sheath 14 may define a sheath orifice 17 and the cannula 34 may define a cannula orifice 19. The orifices 17, 19 may be aligned with the lumen 52 of the adaptor 50 so as to receive a laser 28 and/or a tubing 38 carrying a laser 28. Alternatively, the second opening 58 of the adaptor 50 may align with an opening in the sheath 14 and the laser 28 and/or tubing 38 carrying the laser 28 may enter the first opening 54, may pass through the lumen 52 of the adaptor 50, and may pass through the second opening 58 into the lumen 15 of the sheath 14. The laser 28 and/or tubing 38 carrying the laser 28 may be passed through the lumen 15 of the sheath 14 and exit the sheath 14 at the sheath distal end 26. As mentioned above, the laser 28 and/or tubing 38 carrying the laser 28 may be pre-formed to direct laser energy towards material 32 in the body at a predetermined angle. According to another embodiment, sliding the laser 28 and/or tubing 38 carrying the laser 28 through the adaptor 50 and towards the distal sheath end 26 may alter the angle at which the energy of the laser 28 is directed towards material 32 within the body.

Figure 8A:
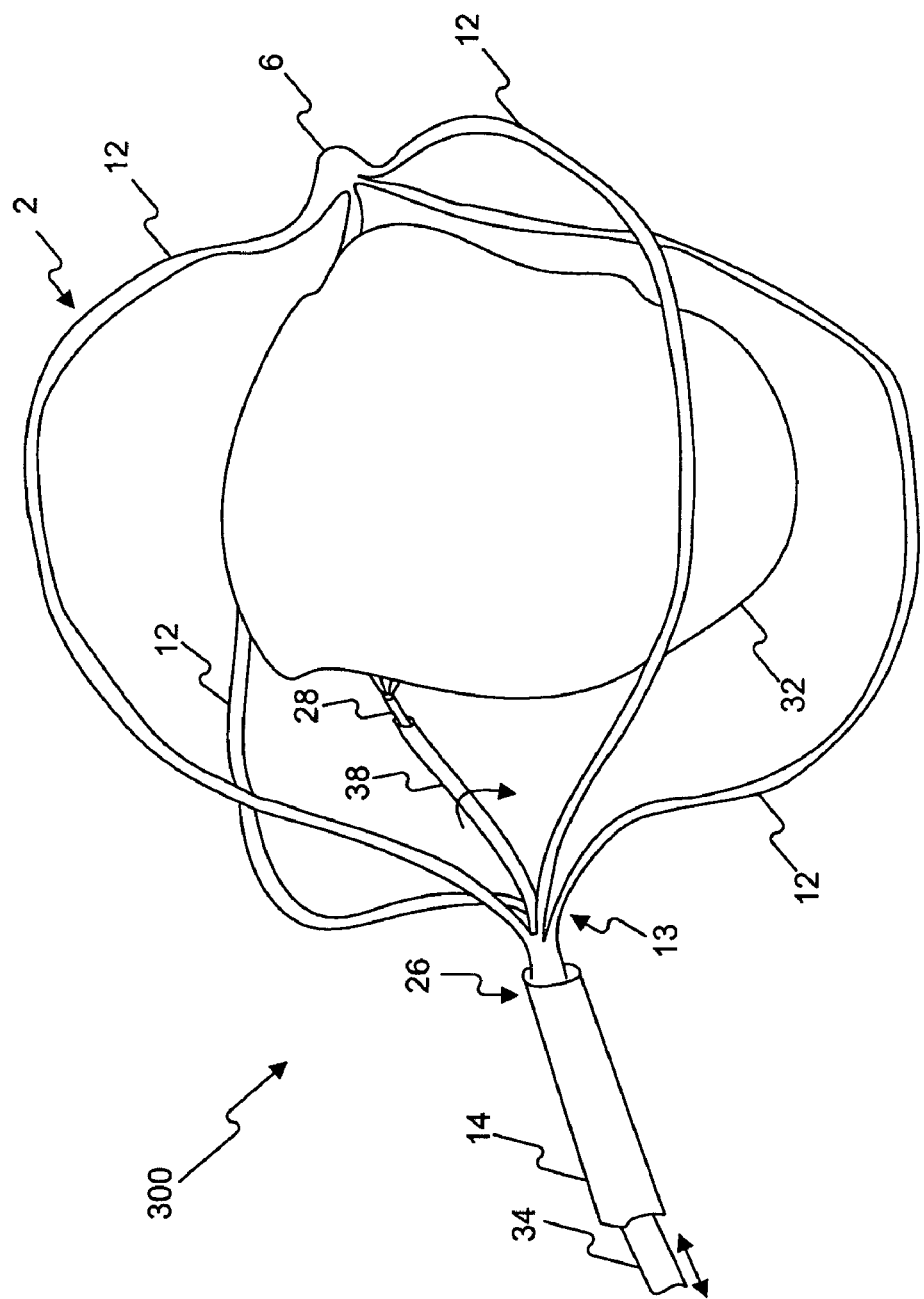
FIG. 8a is an illustrative view of a portion of a retrieval device including a basket having four legs and a laser according to an illustrative embodiment of the invention.
Figure 8B:
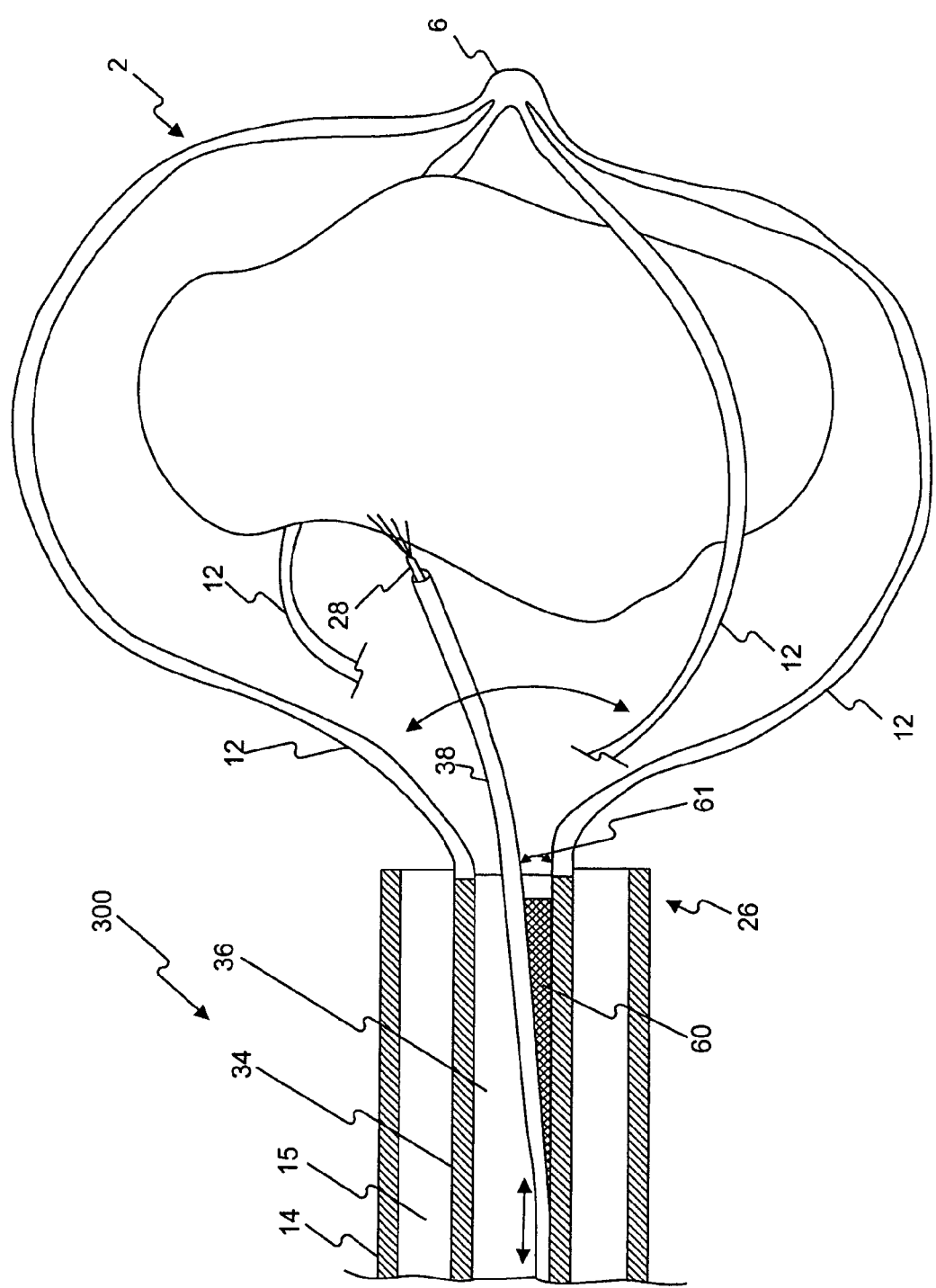
FIG. 8b is a side plan view of the basket depicted in FIG. 8a with the retrieval basket assembly in a fully-extended or open position.
Figure 8C:
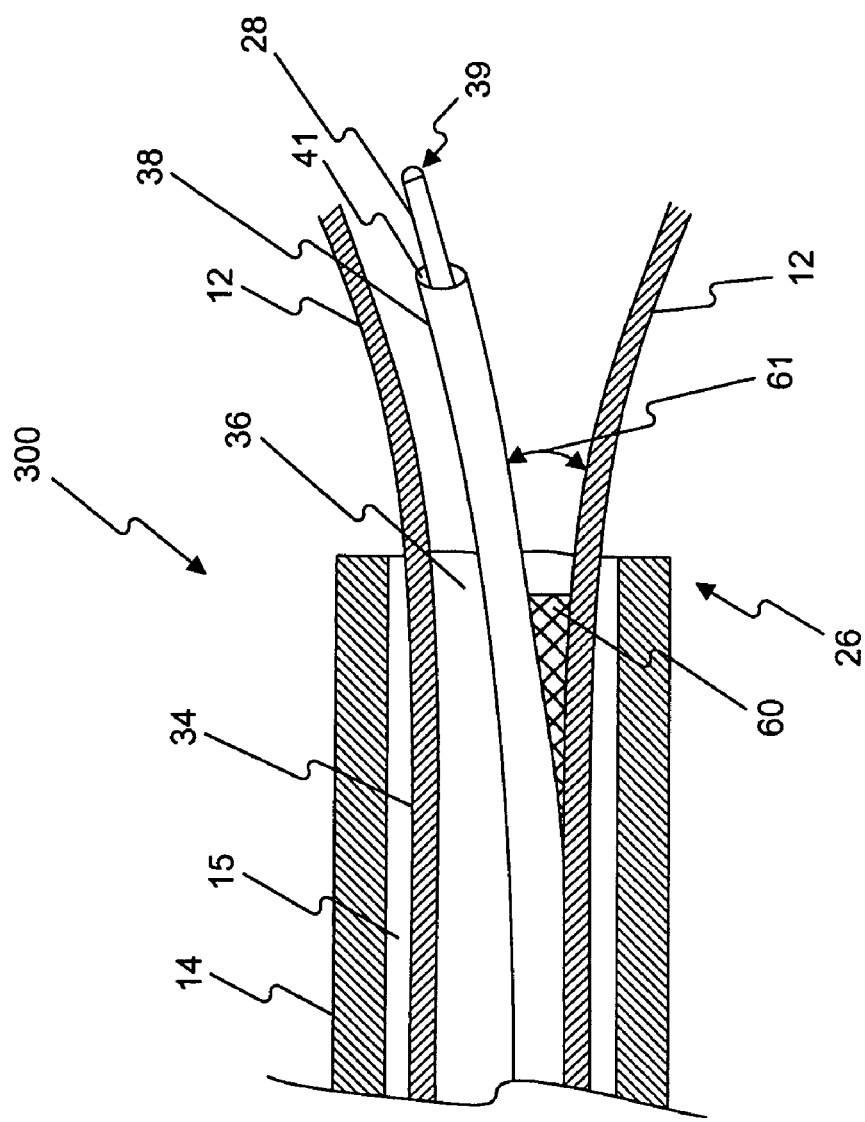
FIG. 8c is an exploded side plan view of a portion of the basket depicted in FIG. 8b.

FIG. 8a is an illustrative view of a retrieval device 300 including a retrieval basket 2 having four legs 12 and a laser 28. FIG. 8b is a side plan view of the basket 2 depicted in FIG. 8b with the retrieval basket assembly 2 in a fully-extended or open position. According to the embodiment illustrated in FIG. 8b, a single piece of hollow cannula 34 defining a lumen 36 may be cut to define four legs 12 of the retrieval basket 2. The hollow cannula 34 may extend within the lumen 15 of the sheath 14 and may exit the sheath distal end 26 when the retrieval basket 2 is in an open and/or fully extended position. FIG. 8c is an exploded side-plan view of a portion of the basket 2 illustrated in FIG. 8b. According to one embodiment, best shown in FIGS. 8 and 8b, the lumen 36 of the hollow cannula 34 may include a ramp 60 for directing the laser 28 and/or tubing 38 carrying the laser 28 to exit the distal sheath end 26 at a predetermined angle 61. The laser 28 and/or tubing 38 carrying the laser 28 may pass through the lumen 36 of the hollow cannula 34 and may be guided by the ramp 60 to exit the lumen 36 at a desired angle 61. The angle 61, relative to the longitudinal axis of the cannula 34, may be in the range of about 0 to 90 degrees, preferably between 20 to 60 degrees.

The size, shape, and angle 61 of the ramp 60 may at least partially determine the angle at which the laser 28 directs its energy at the material 32 within the body. The size and shape of the ramp 60 may vary depending on, for example, the type of procedure performed and the size or shape of the material 32 to be fragmented. In one embodiment, the device 300 may further include a handle 16 and a knob 48 as depicted in FIGS. 5 and 6, and the laser 28 and or tubing 38 carrying the laser 28 may be passed through the distal end 44 of the handle 16 and into the lumen 36 of the cannula 34. In another embodiment, the device 300 may include an adaptor 50 as depicted in FIG. 7, and the laser 28 and/or tubing 38 carrying the laser 28 enters the lumen 36 of the hollow cannula 36 via the adaptor 50.

Figure 9:
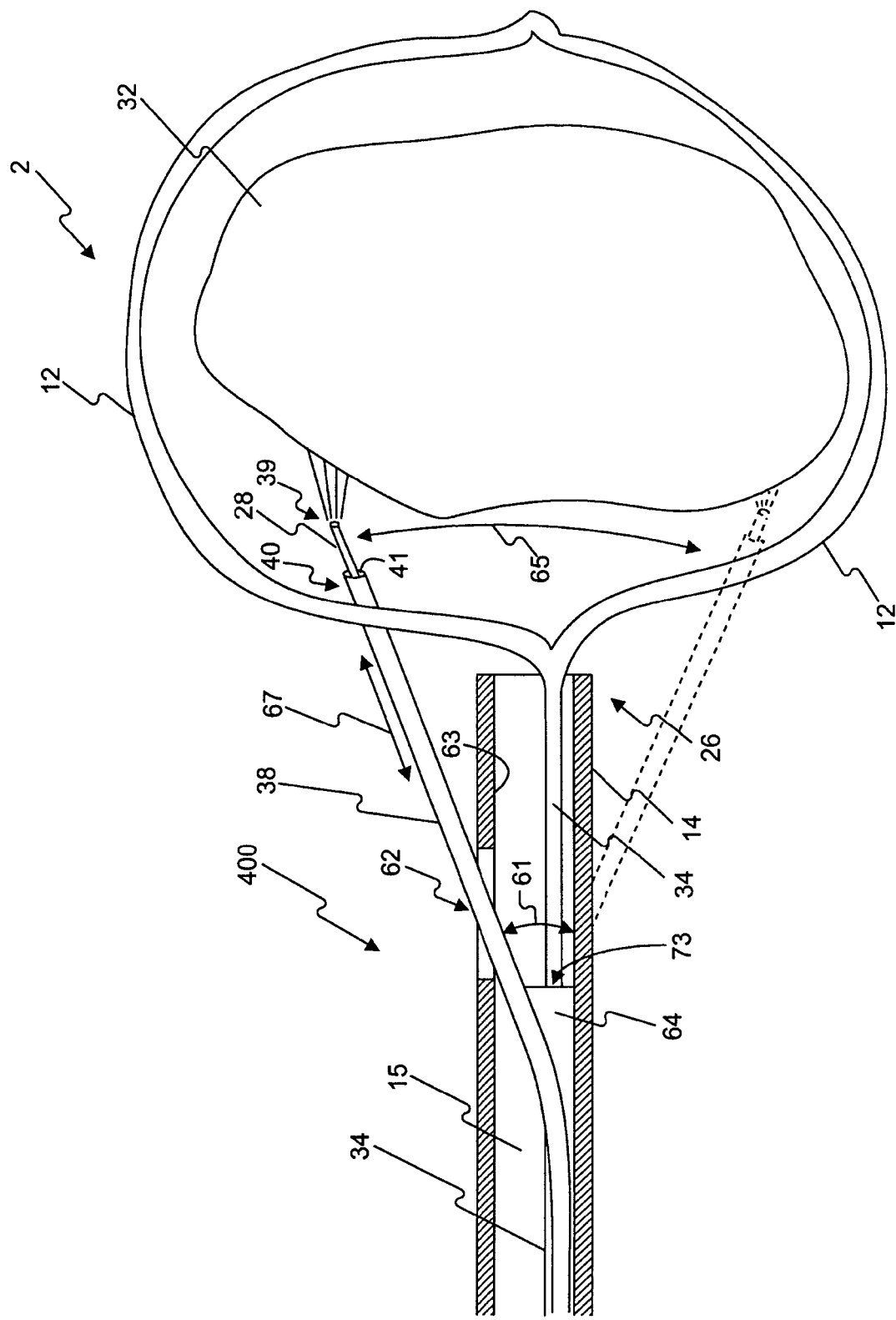
FIG. 9 is a side plan view of a portion of a retrieval device including a basket having two legs and a laser, the retrieval basket assembly being in a fully-extended or open position.

As shown in FIG. 9, in another embodiment of the invention, a device 400 may include a retrieval basket 2 having two legs 12 formed of a single piece of cannula 34. The device 400 may further include a sheath 14 defining at least one lumen 15 and a laser 28 disposed within a hollow tubing 38. A surface 63 of the sheath 14 may include at least one opening 62 and the lumen 15 of the sheath 14 may include a ramp 64 located proximal or adjacent to the at least one opening 62. The ramp 64 may be any ramp-like structure and may be pre-formed to direct the laser 28 and/or tubing 38 carrying the laser 28 at a predetermined angle 61 when the laser 28 and/or tubing 38 carrying the laser 28 may be passed over the ramp 64. The angle 61 relative to the longitudinal axis of the sheath 14 may be in the range of about 0 to 90 degrees, preferably between 20 to 60 degrees. The laser 28 and/or tubing 38 carrying the laser 28 may be passed through the lumen 15 of the sheath 14 and may contact the ramp 64. The laser 28 and/or tubing 38 carrying the laser 28 may be moved toward the proximal end 26 of the sheath 14 and may be directed out of the lumen 15 of the sheath 14 through the at least one opening 62 in the sheath 14. The size and/or shape of the ramp 64 may at least partially determine the angle at which the laser 28 and/or tubing 38 carrying the laser 28 exits the sheath 14 and may at least partially determine the angle at which energy from the laser 28 may be directed towards the material 32. In another embodiment, the laser 28 and/or tubing 38 carrying the laser may be pre-formed to pass over the ramp 64 and out through the at least one opening 62 at the predetermined angle 61. In some embodiments, the ramp 60 may be stamped into the sheath 14 for laser 28 access. As shown in FIG. 9, the cannula 34 may pass through a passage 73 defined by the ramp 60. Such a configuration may provide better visibility of the contrast between the material 32 and the laser 28. The laser 28 may pass coaxially through the cannula 36 until the laser 28 and/or tubing 38 carrying the laser 28 contacts the ramp 60.

In one embodiment of the invention, the laser 28 and/or tubing 38 carrying the laser 28 may be passed through the handle 16 (FIGS. 5-7) of the device 400. In such an embodiment, the laser 28 and/or tubing 38 carrying the laser 28 may be mechanically coupled to a knob 48 such that turning the knob 48 clockwise or counterclockwise may cause a corresponding clockwise or counterclockwise rotation of the laser 28, as indicated by arrow 65 and the dashed lines in FIG. 9. Alternatively, the laser 28 and/or tubing 38 carrying the laser 28 may be mechanically coupled to the sheath 14 such that rotating the sheath 14 clockwise or counterclockwise causes a clockwise or counterclockwise rotation of the laser 28. In another embodiment, both the laser 28 and/or tubing 38 carrying the laser 28 and the sheath 14 may be mechanically coupled to the knob 48 such that turning the knob 48 clockwise or counterclockwise may cause a corresponding clockwise or counterclockwise rotation of the laser 28 and the sheath 14.

In a further embodiment, the laser 28 and/or tubing 38 carrying the laser 28 may enter and may be passed through the lumen 15 of the sheath 14 via an adaptor 50, as shown in FIG. 7. Sliding the laser 28 and/or tubing 38 carrying the laser 28 in a lateral direction towards the distal tip 6 of the basket 2 may alter the direction in which the laser 28 directs energy towards the material 32. In any embodiment, the laser 28 and/or the tubing 38 carrying the laser 28 may be advanced and/or retracted for positioning as shown by arrow 67 in FIG. 9.

Figure 10:
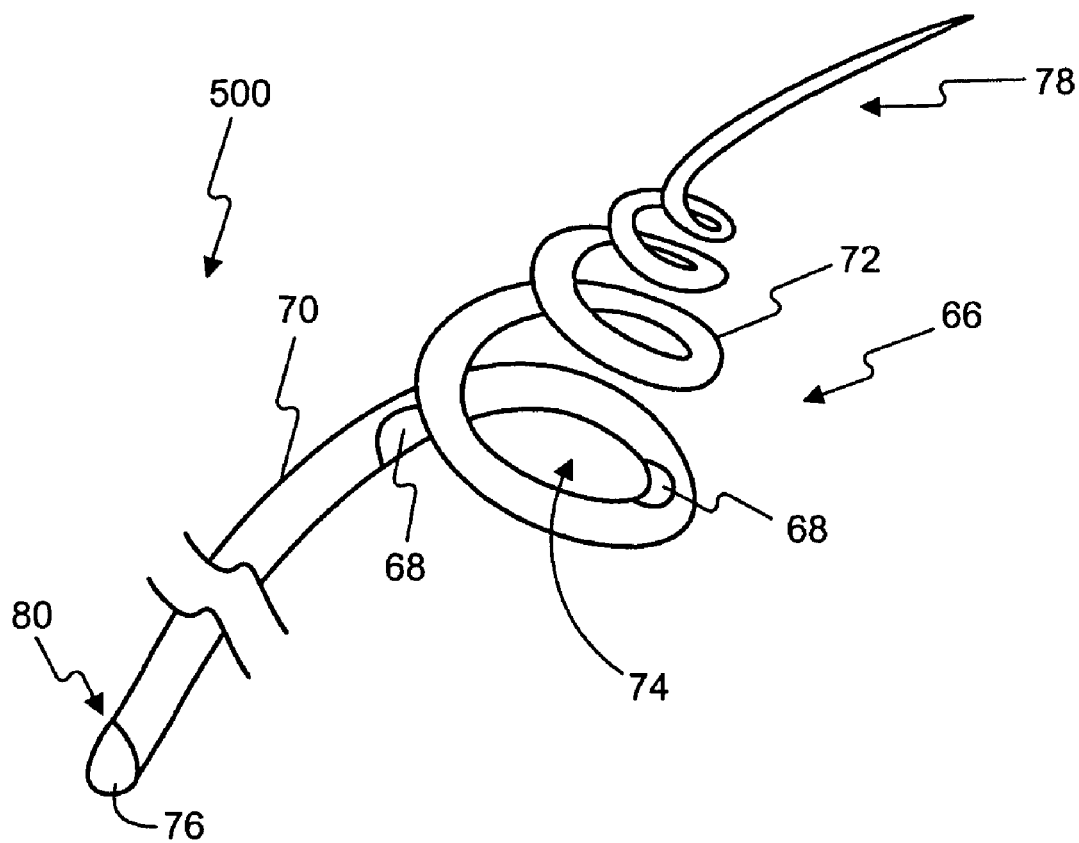
FIG. 10 is an illustrative view of a portion of a medical retrieval device including a stone cone retrieval assembly having two laser exit ports according to one embodiment of the invention.

FIG. 10 illustrates a portion of a device 500 that includes an elongate member 70 and stone cone retrieval assembly 66. The stone cone retrieval assembly 66 may include a core element 72 having a helical shape and a central lumen 74 for retaining and/or capturing material 32 within the body. The core element 72 may also include a plurality of laser exit ports 68. The stone cone retrieval assembly 66 may be formed from hollow tubing or cannula and may include a lumen 76 through which a laser 28 and/or tubing 38 carrying the laser 28 may be passed. The stone cone retrieval assembly 66 may include a distal end 78 and a proximal end 80 that may extend outside of the body when the distal end 78 of the stone cone assembly 66 is inserted into the body to retrieve or fragment material 32.

Figure 11:
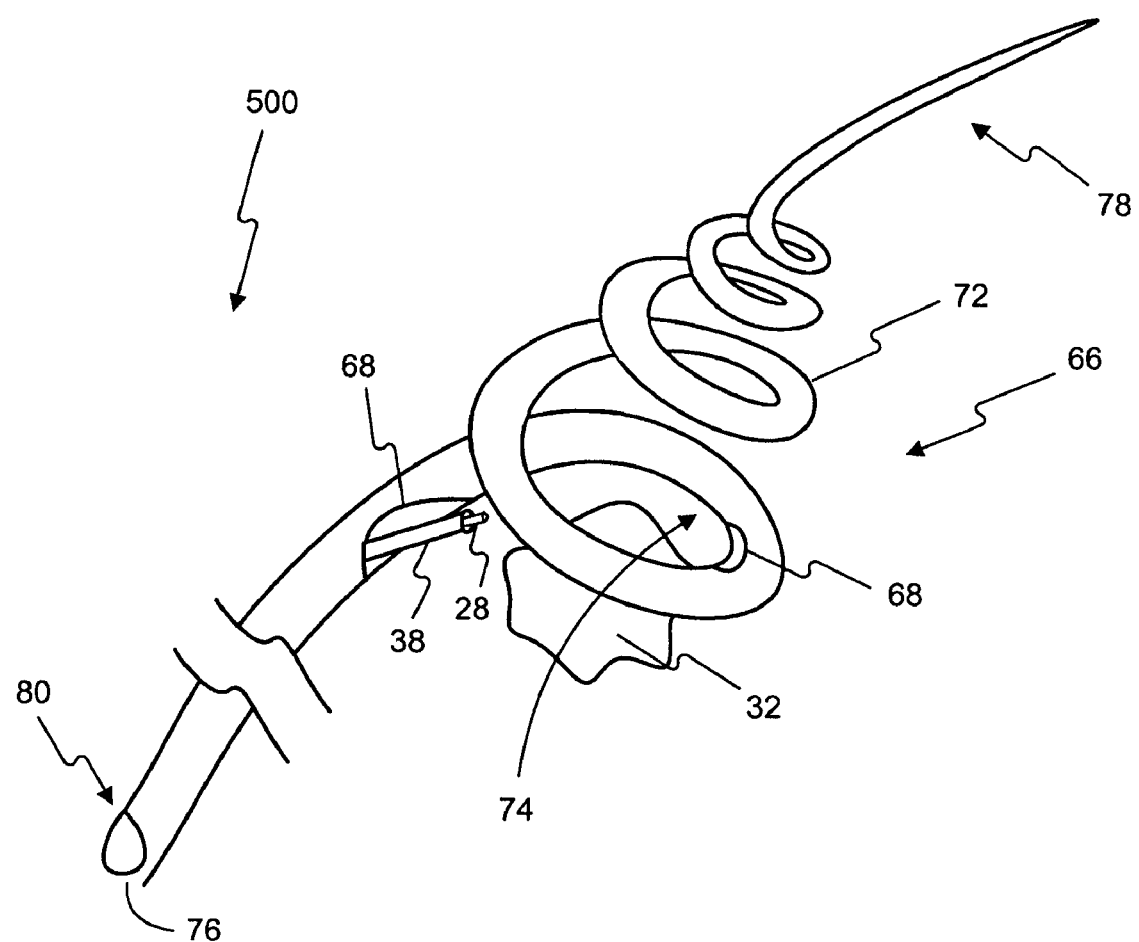
FIG. 11 is an illustrative view of a laser exiting an exit port of the stone cone retrieval assembly of FIG. 10 according to one embodiment of the invention.

As shown in FIG. 11, a laser 28 and/or tubing 38 carrying a laser 28 may be passed through the lumen 76 of the stone cone retrieval assembly 66 and may exit the lumen 76 via one of the plurality of laser exit ports 68. The plurality of exit ports 68 may enable the user to direct energy of the laser 28 at different positions on the material 32. In one embodiment, the laser 28 and/or tubing 38 carrying the laser 28 may be preformed such that the laser 28 and/or tubing 38 carrying the laser 28 may exit the exit port 68 at a predetermined angle. In other embodiments, laterally sliding the laser 28 and/or tubing 38 carrying the laser 28 towards the distal end 78 of the stone cone retrieval assembly 66 may alter the angle at which the laser 28 directs energy toward the material 32.

Figure 12:
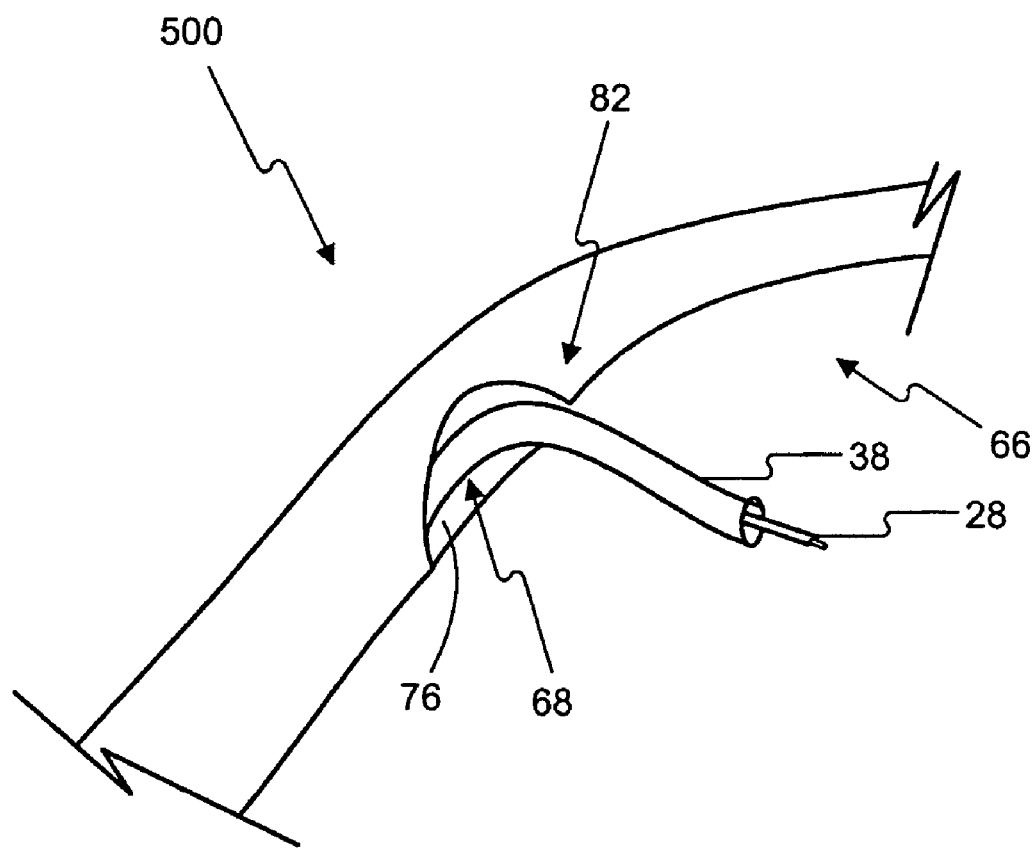
FIG. 12 is an exploded view of an exit port of a medical retrieval device including a stone cone retrieval assembly according to one embodiment of the invention.

As shown in FIG. 12, the size and shape of the exit port 68 may at least partially determine the angle at which the laser 28 directs energy towards the material 32. A lip 82 on the exit port 68 may be shaped to cause the laser 28 and/or tubing 38 carrying the laser 28 to exit the lumen 76 of the stone cone retrieval assembly 66 at a desired angle. During use, the laser 28 and/or tubing 38 carrying the laser 28 may be passed through the lumen 76 of the stone cone retrieval assembly 66 in a distal direction. The laser 28 and/or tubing 38 carrying the laser 28 may contact the lip 82 of the exit port 68 and may be directed out of the exit port 68 at a predetermined angle towards the material 32 within the body. In some embodiments of the invention, the lumen 76 of the stone cone assembly 66 may include a ramp, similar to the ramp of FIG. 8, that directs the laser 28 and/or tubing 38 carrying the laser 28 to exit the exit port 68 at a predetermined angle.

Figure 13:
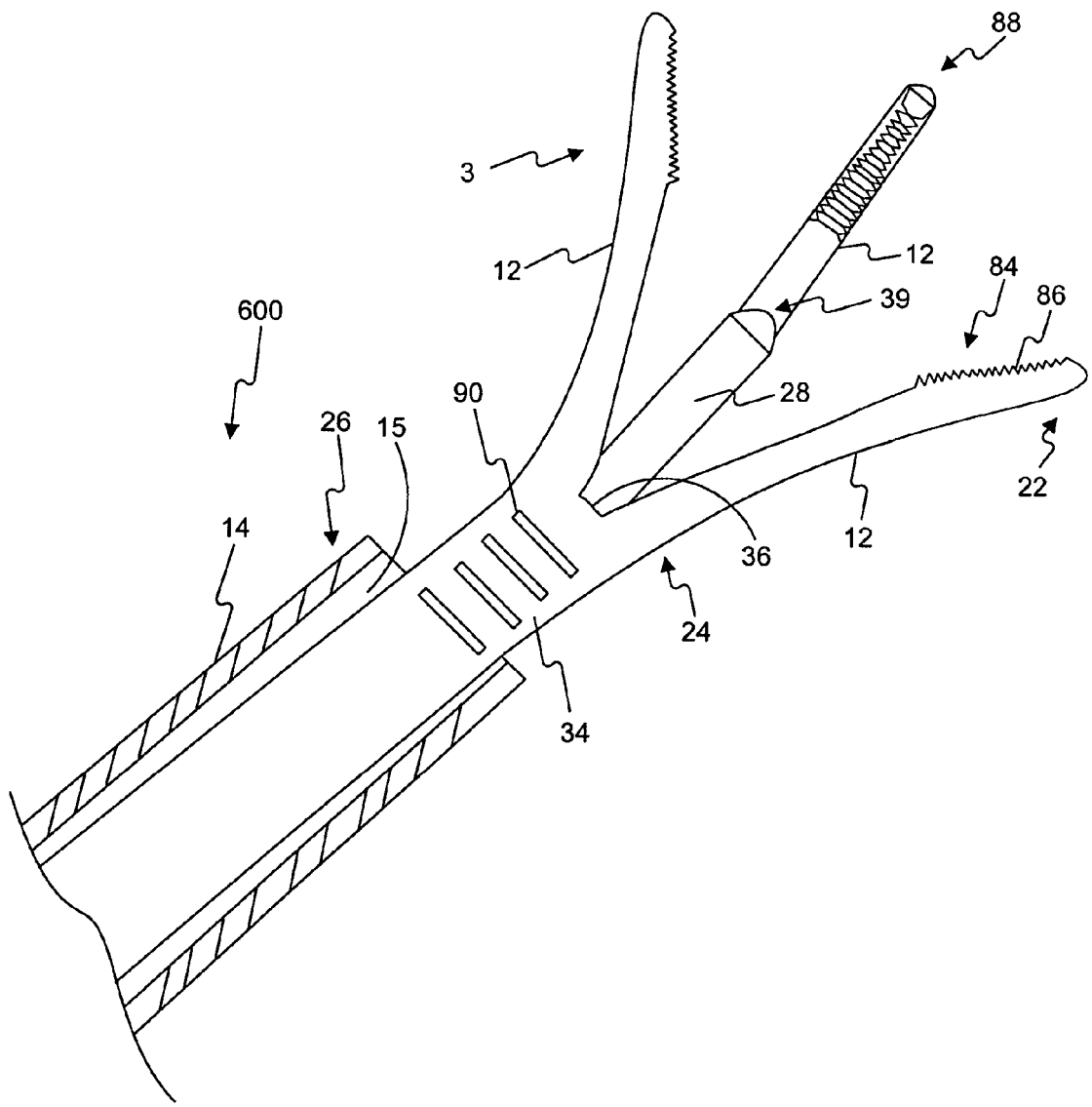
FIG. 13 is a partial cross-sectional view of a medical retrieval device according to another embodiment of the invention.

As shown in FIG. 13, a device 600 of the invention may be formed from a single hollow tube or cannula 34 defining at least one central lumen 36. Similar to other embodiments described above, the cannula 34 may be made of any number of laser resistant, high density polymers such as, for example, PTFE, EPTFE, or Goretex™, or from any number of highly polished laser reflective metals such as, for example, titanium, stainless steel, cobalt chromium, or nitinol. The cannula 34 may also be made from a polymer covered metal, or from any combination of the above materials. In some embodiments, the cannula 34 may include one or more flexibility features 90 located proximate the proximal end 24 of the grasping assembly 3. The flexibility features 90 may be any size or configuration useful in increasing the flexibility of the device 600. In some embodiments, the portions of the cannula 34 may be removed to form the flexibility features 90.

A grasping assembly 3 may be formed from a distal portion of the cannula 34 by cutting, etching, or otherwise removing portions of the cannula 34. Making the grasping assembly 3 out of the same piece of material as the cannula 34 may assist in reducing the overall size and/or profile of the device 3. The grasping assembly 3 may include at least two legs 12 (FIG. 13), each of which have a free end 86. The free end 86 of each leg 12 may be rounded, dulled, or otherwise atraumatic. In some embodiments, the grasping assembly 3 may further include a netting (not shown) attached to the ends 86 of at least two of the legs to provide a backstop for captured material. The netting may be made from the same or similar materials as the cannula 34, and may be made from the same piece of material as the cannula 34 or may be a separate piece of material that is fixedly attached to the legs 12.

The legs 12 may be gradually collapsed to grasp and hold material (not shown) by moving a sheath 14 at least partially over the grasping assembly 3 in a distal direction relative to the assembly 3. The legs 12 may thus be operated in a tweezers-like manner to capture the material. At least one of the legs 12 may include a textured surface 84 to assist in grasping the material. Texture imparted to the surface 84 may be formed, for example, by cutting, etching, sand blasting, or by a variety of other known techniques. These techniques may create any desirable contact feature 86 such as, for example, serrations or pitting useful in gripping and controlling material such as a stone. As shown in FIG. 13, in some embodiments, the textured surface 84 may include teeth 86. The textured surface 84 may be an inner surface of the legs 12 so as to reduce the potential for trauma to body tissue of the patient. The textured surface 84 may also provide multi-point contact with, and substantially perpendicular to, the surface of the material.

The device 600 may also include a laser 28 to assist in fracturing, breaking down, or otherwise reducing the size of material through, for example, laser lithotripsy. The laser 28 may be disposed within the lumen 36 of the cannula 34 and may be moved in a distal direction to obtain access to the material captured by the grasping assembly 3. The laser 28 may be any type of laser known in the art such as, for example, a holmium yag laser. The laser 28 may direct energy toward the material and away from the legs 12 of the grasping assembly 3 once the material is captured. In some embodiments, the device 600 may include a pre-formed tubing (not shown) to carry the laser 28 and direct the laser 28 at a desired angle.

In addition to the devices discussed above, embodiments of the invention relate to methods for breaking up and retrieving material from a body, such as a body tract or body canal. Biological and/or foreign material may be broken up and retrieved from a body by using a retrieval device according to embodiments of the invention. In one embodiment, the retrieval device may include a basket retrieval assembly 2 comprising a distal tip 6 that assists in the capture of material that may be located within the body and a laser 28 that directs energy towards the material at a predetermined angle to fragment or break up the material prior to removal of the device and/or material from the body.

The retrieval device may be inserted into the body and the basket retrieval assembly 2 may be moved into the unrestrained position. The unrestrained or expanded position may be achieved by withdrawing the sheath 14 from the basket retrieval assembly 2 with the retrieval assembly 2 in a stationary position or by extending the retrieval assembly 2 outside the sheath 14 with the sheath 14 in a stationary position. Once expanded, the retrieval assembly 2 may be maneuvered via an actuator 4 on the handle 16 (which may be located outside of the body) of the retrieval device until the material 32 is entrapped within the three-dimensional retrieval assembly 2. The material 32 may be captured within the retrieval assembly 2 by moving the retrieval assembly 2 relative to the sheath 14 by any of the above disclosed mechanisms to close the legs 12 of the retrieval assembly 2 around the material 32. With the material 32 held by the retrieval assembly 2, a laser 28 may be positioned according to any of the above embodiments to direct energy toward the material 32 at an angle 61 that is relative to a longitudinal axis of the retrieval device. The angle 61 relative to the longitudinal axis may range from approximately 0 to approximately 90 degrees, and the laser 28 may assist in fragmenting the material 32. The laser 28 and the medical retrieval device including the retrieval assembly 2, may be withdrawn from the body to remove the material 32 from the body.

In other embodiments, the retrieval device may be positioned within the body to direct energy from the laser 28 towards the material 32 and move the material 32 in the direction of and into the three-dimensional basket retrieval assembly 2. Closing the legs 12 of the basket assembly 2 allows the device to capture and remove the fragmented material 32. In another embodiment, the retrieval device comprising a stone cone retrieval assembly 66 and a laser 28 may be positioned within the body for fragmenting material 32 before capturing material 32 in the stone cone 66 and removing the material 32 and the device from within the body.

Additional mechanisms for breaking up material 32 before its removal from the body may be part of the retrieval devices or additional tools/devices can also be inserted into the body and utilized at the appropriate time to break apart the material 32.

Variations, modifications, and other implementations of what is described herein will occur to those of ordinary skill without departing from the spirit and the scope of the invention. Accordingly, the invention is not to be limited only to the preceding illustrative description. It is intended that the specification and examples be considered as exemplary only, with a true scope and spirit of the invention being indicated by the following claims.

What is claimed is:

1. A medical device, comprising;
   a sheath having a lumen;
   an elongate member disposed within the lumen of the sheath and moveable relative to the sheath, the elongate member including a retrieval assembly having a collapsed position within the lumen of the sheath and an expanded position when extended beyond a distal end of the sheath, wherein the retrieval assembly includes a plurality of legs;
   a laser disposed within a lumen of the elongate member, the laser and the elongate member being moveable relative to each other; and
   wherein the elongate member defines an inner surface angled relative to a longitudinal axis of the elongate member to direct the laser at a predetermined angle relative to the longitudinal axis of the elongate member.

2. The device of claim 1, further including a handle having an actuation mechanism configured to assist in transitioning the retrieval assembly between the collapsed position and the expanded position.

3. The device of claim 2, wherein at least one of the elongate member or the sheath is connected to the actuation mechanism to provide relative movement between the elongate member and the sheath.

4. The device of claim 2, wherein the handle further includes a knob operatively connected to the laser to assist in manipulating the laser.

5. The device of claim 4, wherein the knob is configured to rotate the laser relative to the sheath and the elongate member.

6. The device of claim 5, wherein the knob is configured to translate the laser longitudinally relative to the sheath and the elongate member.

7. The device of claim 2, wherein the handle further includes an adaptor defining an adaptor lumen configured to receive the laser.

8. The device of claim 7, wherein the sheath defines an orifice aligned with the adaptor lumen and configured to receive the laser.

9. The device of claim 1, wherein at least one of the plurality of legs includes a free distal end, the at least one of the plurality of legs defining a portion of the lumen of the elongate member configured to receive the laser.

10. The device of claim 9, wherein the at least one of the plurality of legs comprises a preformed shape and exits the sheath at the predetermined angle.

11. The device of claim 9, wherein the laser is disposed within the portion of the lumen of the at least one of the plurality of legs and moveable relative to the at least one of the plurality of legs.

12. The device of claim 11, wherein the laser exits the free distal end of the at least one of the plurality of legs to deliver energy to a material at the predetermined angle.

13. The device of claim 1, wherein the laser comprises a pre-formed shape and exits the lumen of the elongate member at the predetermined angle.

14. The device of claim 1, wherein the predetermined angle is between approximately 20 degrees and approximately 60 degrees relative to the longitudinal axis of the elongate member.

15. The device of claim 1, wherein the laser includes a laser cannula.

16. The device of claim 1, wherein each of the plurality of legs is joined at a distal tip of the retrieval assembly.

17. The device of claim 1, wherein each of the plurality of legs includes a free distal end, the plurality of legs being formed by removing at least a portion of the elongate member.

18. The device of claim 17, wherein at least a portion of the elongate member proximal to the plurality of legs is removed to increase the flexibility of the device.

19. The device of claim 17, wherein at least one of the plurality of legs includes a textured surface to assist in gripping a material.

20. The device of claim 19, wherein the textured surface includes teeth on an inner surface of the at least one of the plurality of legs.

21. A medical device, comprising:
    a sheath including a lumen, a first opening on a distal most end of the sheath, a second opening on a side surface of the sheath at a distal end of the sheath, and an inner surface proximate the second opening to direct a laser through the second opening; and
    an elongate member disposed within the lumen of sheath and moveable relative to the sheath, the elongate member including a retrieval assembly having a collapsed position within the lumen of the sheath and an expanded position when extended beyond the first opening of the sheath.

22. The device of claim 21, wherein the retrieval assembly comprises a first leg, a second leg, and a tip joining the first and second legs together.

23. The device of claim 21, wherein the inner surface is angled relative to a longitudinal axis of the sheath.

24. The device of claim 21, further including a laser disposed within the lumen of the sheath.

25. The device of claim 24, wherein a ramp-like structure defines the inner surface.

26. The device of claim 25, wherein the ramp-like structure is configured to direct the laser at an angle between approximately 20 degrees and approximately 60 degrees relative to a longitudinal axis of the sheath.

27. The device of claim 25, wherein at least a portion of the elongate member is disposed within a passage of the ramp-like structure, the elongate member being movable relative to the ramp-like structure.

28. The device of claim 24, wherein the laser is disposed within a laser cannula and is moveable relative to the laser cannula.

29. The device of claim 28, wherein the inner surface is positioned to direct the laser cannula to exit the lumen of the sheath through the second opening at a predetermined angle relative to a longitudinal axis of the sheath.

* * * * *

UNITED STATES PATENT AND TRADEMARK OFFICE
CERTIFICATE OF CORRECTION

PATENT NO. : 7,727,227 B2
APPLICATION NO. : 10/942084
DATED : June 1, 2010
INVENTOR(S) : James A. Teague et al.

It is certified that error appears in the above-identified patent and that said Letters Patent is hereby corrected as shown below:

Claim 21, col. 16, line 29, "distal most" should read --distalmost--.

Signed and Sealed this

Twentieth Day of July, 2010

David J. Kappos
*Director of the United States Patent and Trademark Office*